US012672619B2

(12) United States Patent
Morris et al.

(10) Patent No.: US 12,672,619 B2
(45) Date of Patent: Jul. 7, 2026

(54) METHODS AND COMPOSITIONS FOR DEVELOPING CEREAL VARIETIES WITH CHILLING TOLERANCE

(71) Applicant: Kansas State University Research Foundation, Manhattan, KS (US)

(72) Inventors: Geoffrey P. Morris, Manhattan, KS (US); Terry Felderhoff, Manhattan, KS (US); Sandeep Marla, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 466 days.

(21) Appl. No.: 17/906,657

(22) PCT Filed: Mar. 22, 2021

(86) PCT No.: PCT/US2021/023416
§ 371 (c)(1),
(2) Date: Sep. 19, 2022

(87) PCT Pub. No.: WO2021/189034
PCT Pub. Date: Sep. 23, 2021

(65) Prior Publication Data
US 2023/0292686 A1      Sep. 21, 2023

Related U.S. Application Data

(60) Provisional application No. 62/992,508, filed on Mar. 20, 2020.

(51) Int. Cl.
*A01H 1/00*        (2006.01)
*A01H 6/46*        (2018.01)
*C12Q 1/6895*    (2018.01)

(52) U.S. Cl.
CPC ......... *A01H 1/1225* (2021.01); *A01H 6/4666* (2018.05); *C12Q 1/6895* (2013.01); *C12Q 2600/13* (2013.01)

(58) Field of Classification Search
None
See application file for complete search history.

(56) References Cited

U.S. PATENT DOCUMENTS

2019/0153546 A1      5/2019  Gelli et al.

OTHER PUBLICATIONS

Miller, Frederick R., and Sorghum Breeder. "The breeding of sorghum." Biology and Breeding for Resistance to Arthropods and Pathogens in Agricultural Plants. Proc. Inter. Short Course in Host Plant Resistance. July (1979): 128-136. (Year: 1979).*

Cisse, N'Diaga, and Gebisa Ejeta. "Genetic variation and relationships among seedling vigor traits in sorghum." Crop Science 43.3 (2003): 824-828. (Year: 2003).*

Collard, Bertrand CY, et al. "An introduction to markers, quantitative trait loci (QTL) mapping and marker-assisted selection for crop improvement: the basic concepts." Euphytica 142 (2005): 169-196. (Year: 2005).*

Knoll, Joseph, Nilupa Gunaratna, and Gebisa Ejeta. "QTL analysis of early-season cold tolerance in sorghum." Theoretical and Applied Genetics 116 (2008): 577-587. (Year: 2008).*

Perumal, R., et al. "Registration of nine grain sorghum seed parent (A/B) lines." Journal of Plant Registrations 9.2 (2015): 244-248. (Year: 2015).*

Singh, A. and A. Singh. 2016. Breeding Methods. In Crop Improvement, interactive e-learning courseware. Plant Breeding E-Learning in Africa. Retrieved from https://pbea.agron.iastate.edu on Nov. 13, 2025 (Year: 2016).*

Burow, G. B., et al. "Registration of the BTx623/IS3620C recombinant inbred mapping population of sorghum." Journal of Plant Registrations 5.1 (2011): 141-145. (Year: 2011).*

Knoll, Joseph, and Gebisa Ejeta. "Marker-assisted selection for early-season cold tolerance in sorghum: QTL validation across populations and environments." Theoretical and Applied Genetics 116 (2008): 541-553. (Year: 2008).*

Marla et al., "Genetic Architecture of Chilling Tolerance in Sorghum Dissected with a Nested Association Mapping Population," G3: Genes, Genomes, and Genetics, vol. 9, Dec. 2019, pp. 4045-4057.

* cited by examiner

*Primary Examiner* — Amjad Abraham
*Assistant Examiner* — Kelsey L McWilliams
(74) *Attorney, Agent, or Firm* — McKee, Voorhees & Sease, PLC

(57)        ABSTRACT

Disclosed herein are markers which are associated with chilling tolerance and provide for breeding methods to identify such plants to integrate this trait into cereal plants and further to identify analogous markers in other cereal plants. Importantly, these markers are not linked with deleterious traits such as tall plant height or tannin content, providing for the creation of plant varieties and elite plant varieties with chilling tolerance, dwarf plant height and lack of tannins.

2 Claims, 7 Drawing Sheets

Specification includes a Sequence Listing.

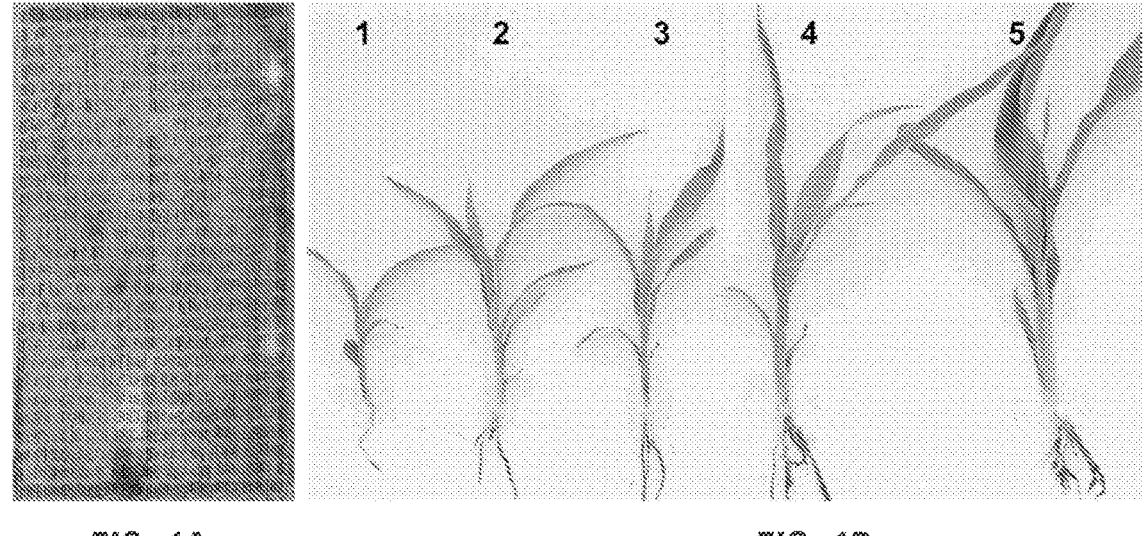
*FIG. 1A* *FIG. 1B*
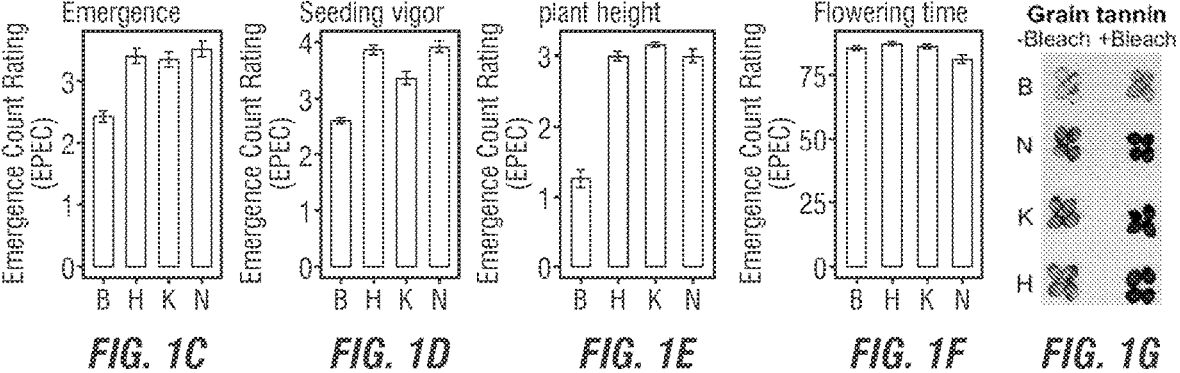
*FIG. 1C* *FIG. 1D* *FIG. 1E* *FIG. 1F* *FIG. 1G*

METHODS AND COMPOSITIONS FOR DEVELOPING CEREAL VARIETIES WITH CHILLING TOLERANCE

CROSS REFERENCE TO RELATED APPLICATIONS

This is a U.S. National Phase application claiming priority to PCT/US2021/23416, filed Mar. 22, 2021, which claims priority to provisional application U.S. Ser. No. 62/992,508 filed Mar. 20, 2020, herein incorporated by reference in their entireties.

GRANT REFERENCE

This invention was made with government support under the United States Department of Agriculture research grant 2014-38502-22598. The government has certain rights in the invention

SEQUENCE LISTING

The instant application contains a Sequence Listing which has been submitted in ASCII format by electronic submission and is hereby incorporated by reference in its entirety. Said ASCII copy, created on Mar. 19, 2021, is named 2021-03-19_MORRIS_P13118W000_SEQLISTING_ST25.txt and is 18,749 bytes in size.

FIELD OF THE INVENTION

The present invention relates to the field of plant breeding and, more specifically, to methods and compositions for producing cereal and grain varieties such as sorghum with chilling tolerance.

BACKGROUND OF THE INVENTION

Cold temperatures are a major factor limiting plant productivity globally for both wild plants and crops. Tropical-origin crops (e.g. maize, rice, tomato, cotton, sorghum) are typically sensitive to chilling temperatures (0-15°, which limits their range and/or growing season in temperate climates. Developing chilling-tolerant varieties could facilitate early planting to extend growing seasons, prevent soil moisture depletion, and shift growth and flowering to more favorable evapotranspirative conditions. For breeding chilling tolerance in tropical-origin crops, chilling-adapted germplasm from high-latitude zones and high-altitude tropical regions can be targeted as donors.

Sorghum, a tropical-origin warm-season (C4) cereal, is among the major crops that are generally susceptible to chilling. Sorghum originated in tropical Africa (c. 5-10 thousand years ago) and diffused to temperate areas, including China (c. 800 years ago) and the United States (c. 200 years ago). Diffusion of tropical sorghums to temperate climates has led to commercial sorghum industries covering several million hectares in US, Australia, Argentina, and China. Using a phytogeographic approach, Chinese sorghum were targeted as chilling tolerance donors for conventional breeding starting in the 1960s. However, characteristics of Chinese sorghums that are undesirable for US grain sorghum, particularly grain tannins and tall stature (>2 m), have hampered breeding. Biparental linkage mapping identified chilling tolerance QTL tagged by the same molecular markers as grain tannins and plant height, but small populations and low marker density limited dissection of these traits.

SUMMARY OF THE INVENTION

The invention provides cereal plants such as sorghum with improved chilling tolerance (plants with tolerance at temperatures from about 1 to about 18° C.). Markers have been identified which are associated with this trait and provide for breeding methods to identify such plants to integrate this trait into cereal plants and further to identify analogous markers in other cereal plants. Importantly, applicants have broken the linkage of chilling tolerance with deleterious traits such as tall plant height or tannin content, providing for the creation of plant varieties and elite plant varieties with chilling tolerance, dwarf plant height and lack of tannins. In some embodiments, the plant comprises one or more chilling tolerance QTL introgressed in its genome. In some embodiments, the locus is one or more of qSbCT01.06, qSbCT01.13, qSbCT01.57, qSbCT02.08, qSbCT04.62, qSbCT05.04, qSbCT07.10, qSbCT07.59, and qSbCT09.57. Preferably, the plants comprise an inactivated tan1 and/or tan2 allele to provide an absence of grain tannins. Preferably, the plants comprise a dwarf phenotype from other than dw1 and/or dw3 allele to provide a short stature phenotype. In some embodiments, the chilling tolerance is derived from the sorghum cultivar KS-090-CT13 or KS-105-CT124 described herein. In some embodiments, the chilling tolerance is derived from the Chinese sorghum cultivars Hong Ke Zi, Kaoliang, or Niu Sheng Zui. Preferably, the sorghum plant is an elite line. In some embodiments, the plant is the sorghum cultivar KS-090-CT13 or KS-105-CT124. The chilling tolerance loci described herein can be used to identify analogous loci and corresponding gene(s) to provide chilling tolerance in other chilling sensitive monocotyledonous cereal plants such as, but not limited to, maize, pearl millet, rice, and sugarcane.

Compositions and methods for introgressing a chilling tolerance locus into chilling sensitive sorghum plants without introgressing undesirable grain tannin and tall stature traits are provided herein. In one embodiment, the methods comprise providing a first sorghum plant with the chilling tolerance locus, providing a second sorghum plant, crossing the first sorghum plant with the second first sorghum plant to produce a population of sorghum progeny plants, and selecting from the population at least one sorghum plant having the chilling tolerance locus. In some embodiments, the locus is one or more of qSbCT01.06, qSbCT01.13, qSbCT01.57, qSbCT02.08, qSbCT04.62, qSbCT05.04, qSbCT07.10, qSbCT07.59, and qSbCT09.57. The methods may further comprise selecting from the population at least one sorghum plant having an inactivated tan1 and/or tan2 allele. The methods may further comprise selecting from the population at least one sorghum plant having a dwarf phenotype from other than dw1 and/or dw3 allele. In some embodiments, the methods comprise performing additional backcrosses and selections. Preferably, the introgressing comprises marker assisted selection for one or more loci associated with chilling tolerance. In some embodiments, the first sorghum plant is sorghum cultivar Hong Ke Zi, Kaoliang, or Niu Sheng Zu. Chilling tolerant sorghum plants obtained by the methods are also provided. Preferably, the chilling tolerant sorghum plants obtained also exhibit a short stature and lack grain tannins.

Compositions and methods for identifying and/or selecting (i.e. obtaining) sorghum plants having increased chilling tolerance are provided herein. In one embodiment, a method of identifying a sorghum plant comprising at least one locus associated with chilling tolerance is provided, the method comprises the steps of: a) genotyping at least one sorghum plant with at least one sorghum nucleic acid marker, wherein the marker is one or more of S1_5730743, S1_6902771, S1_9756192, S1_13188261, S1_13526795, S1_57941435, S2_8672301, S2_9218398, S2_9260382, S4_60623655, S4_61096729, S4_61680898, S4_62368531, S4_62380875, S4_62455479, S4_62682585, S5_4284787, S5_4403613, S7_8916696, S7_12580350, S7_59290017, S7_59915577, S9_55625332, and S9_58070153, or a marker within 1 cM, 2 cM, or 5 cM thereof; and b) selecting at least one sorghum plant comprising an allele of at least one of the nucleic acid markers that is associated with chilling tolerance. Preferably, the at least one sorghum plant genotyped in step a) and/or the at least one sorghum plant selected in step b) is a sorghum plant from a population generated by a cross. Preferably, the population is generated by a cross of at least one chilling tolerant sorghum plant with at least one chilling sensitive sorghum plant. In some embodiments, the selected one or more sorghum plants exhibit chilling tolerance, a short stature, and lack grain tannins. The methods may further comprise the step of c) assaying the selected sorghum plant for chilling tolerance.

In another embodiment, a method of identifying and/or selecting a sorghum plant with chilling tolerance is provided, the method comprising the steps of: a) screening a population with a marker to determine if one or more sorghum plants from the population comprises a locus associated with chilling tolerance; and b) selecting from the population at least one sorghum plant comprising the locus. Preferably, the locus is one or more of qSbCT01.06, qSbCT01.13, qSbCT01.57, qSbCT02.08, qSbCT04.62, qSbCT05.04, qSbCT07.10, qSbCT07.59, and qSbCT09.57. Preferably, the marker is one or more of S1_5730743, S1_6902771, S1_9756192, S1_13188261, S1_13526795, S1_57941435, S2_8672301, S2_9218398, S2_9260382, S4_60623655, S4_61096729, S4_61680898, S4_62368531, S4_62380875, S4_62455479, S4_62682585, S5_4284787, S5_4403613, S7_8916696, S7_12580350, S7_59290017, S7_59915577, S9_55625332, and S9_58070153, or a marker within 1 cM, 2 cM, or 5 cM thereof. The methods may further comprise the steps of c) crossing the sorghum plant of b) to a second sorghum plant; and d) obtaining a progeny plant that has the chilling tolerance locus.

In another embodiment, a method of selecting a sorghum plant with chilling tolerance is provided, the method comprising: a) obtaining a first sorghum plant that comprises within its genome a locus associated with chilling tolerance, wherein the locus is one or more of qSbCT01.06, qSbCT01.13, qSbCT01.57, qSbCT02.08, qSbCT04.62, qSbCT05.04, qSbCT07.10, qSbCT07.59, and qSbCT09.57; b) crossing the first sorghum plant to a second sorghum plant; c) evaluating progeny plants for the presence of the locus; and d) selecting a progeny plant that has the locus. In some embodiments, the evaluating comprises genotyping the progeny plant with at least one sorghum nucleic acid marker. Preferably, the marker is one or more of S1_5730743, S1_6902771, S1_9756192, S1_13188261, S1_13526795, S1_57941435, S2_8672301, S2_9218398, S2_9260382, S4_60623655, S4_61096729, S4_61680898, S4_62368531, S4_62380875, S4_62455479, S4_62682585, S5_4284787, S5_4403613, S7_8916696, S7_12580350, S7_59290017, S7_59915577, S9_55625332, and S9_58070153, or a marker within 1 cM, 2 cM, or 5 cM thereof.

BRIEF DESCRIPTION OF THE FIGURES

FIG. 1 shows Chinese sorghums harbor early-season chilling tolerance and characteristics undesirable for US grain sorghums. (A) Aerial image of an early-planted field (AB17) trial for chilling tolerance phenotyping based on stitched RGB imagery (B) Seedling vigor rating used in field trials. In early-planted field trials, differences were observed in (C) emergence and (D) seedling vigor between the four NAM founders, B (BTx623), K (Kao), H (HKZ), and N (NSZ). Additionally, (E) significant variation in plant height at maturity, (F) no significant difference in flowering time (days after emergence), and (G) presence/absence variation in grain tannins were observed.

DETAILED DESCRIPTION OF THE INVENTION

Figure 2A:
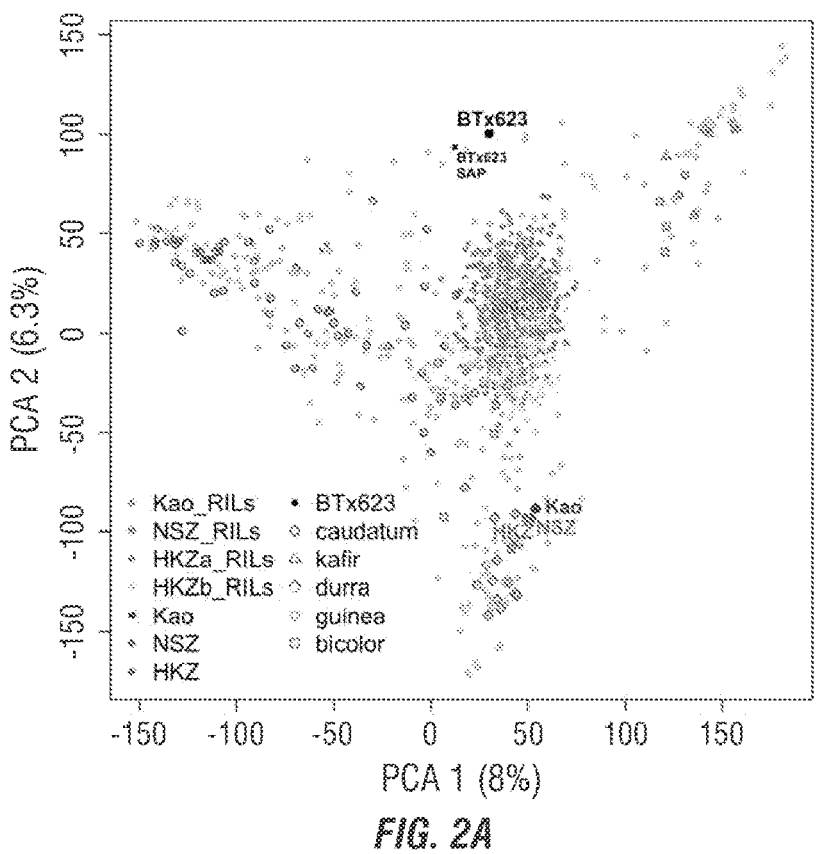
FIG. 2 shows genetic properties of the chilling NAM population. (A) Principal component analysis (PCA) of the NAM ($n_{RIL}$=771) plotted on PCA axes built with 401 accessions of the global sorghum diversity germplasm. Major botanical races (Caudatum, Kafir, Durra, Guinea, and Bicolor) of global accessions are noted with symbols (B) Linkage disequilibrium (LD) decay of the NSZ, HKZa, HKZb, and Kao families. LD decay rate of diverse accessions from China (n=29) and Ethiopia (n=176) are presented for comparison.

The present invention now will be described more fully with reference to the accompanying examples. The invention may be embodied in many different forms and should not be construed as limited to the embodiments set forth in this application; rather, these embodiments are provided so that this disclosure will satisfy applicable legal requirements.

Many modifications and other embodiments of the invention will come to mind to one skilled in the art to which this invention pertains, having the benefit of the teachings presented in the descriptions and the drawings herein. As a result, it is to be understood that the invention is not to be limited to the specific embodiments disclosed and that modifications and other embodiments are intended to be included within the scope of the appended claims. Although specific terms are used in the specification, they are used in a generic and descriptive sense only and not for purposes of limitation.

The following definitions and introductory matters are provided to facilitate an understanding of the present invention.

Numeric ranges recited within the specification, including ranges of "greater than," "at least," or "less than" a numeric value, are inclusive of the numbers defining the range and include each integer within the defined range.

The singular terms "a", "an", and "the" include plural referents unless context clearly indicates otherwise. Similarly, the word "or" is intended to include "and" unless the context clearly indicate otherwise. The word "or" means any one member of a particular list and also includes any combination of members of that list.

The term "allele" refers to one of two or more different nucleotide sequences that occur at a specific locus.

"Allele frequency" refers to the frequency (proportion or percentage) at which an allele is present at a locus within an individual, within a line, or within a population of lines. For example, for an allele "A", diploid individuals of genotype "AA", "Aa", or "aa" have allele frequencies of 1.0, 0.5, or 0.0, respectively. One can estimate the allele frequency within a line by averaging the allele frequencies of a sample of individuals from that line. Similarly, one can calculate the allele frequency within a population of lines by averaging the allele frequencies of lines that make up the population. For a population with a finite number of individuals or lines, an allele frequency can be expressed as a count of individuals or lines (or any other specified grouping) containing the allele.

An "amplicon" is an amplified nucleic acid, e.g., a nucleic acid that is produced by amplifying a template nucleic acid by any available amplification method (e.g., PCR, LCR, transcription, or the like).

The term "amplifying" in the context of nucleic acid amplification is any process whereby additional copies of a selected nucleic acid (or a transcribed form thereof) are produced. Typical amplification methods include various polymerase based replication methods, including the polymerase chain reaction (PCR), ligase mediated methods such as the ligase chain reaction (LCR) and RNA polymerase based amplification (e.g., by transcription) methods.

An allele is "associated with" a trait when it is part of or linked to a DNA sequence or allele that affects the expression of the trait. The presence of the allele is an indicator of how the trait will be expressed.

"Backcrossing" refers to the process whereby hybrid progeny are repeatedly crossed back to one of the parents. In a backcrossing scheme, the "donor" parent refers to the parental plant with the desired gene/genes, locus/loci, or specific phenotype to be introgressed. The "recipient" parent (used one or more times) or "recurrent" parent (used two or more times) refers to the parental plant into which the gene or locus is being introgressed. For example, see Ragot, M. et al. (1995) Marker-assisted backcrossing: a practical example, in Techniques et Utilisations des Marqueurs Moléculaires Les Colloques, Vol. 72, pp. 45-56, and Openshaw et al., (1994) Marker-assisted Selection in Backcross Breeding, Analysis of Molecular Marker Data, pp. 41-43. The initial cross gives rise to the F1 generation; the term "BC1" then refers to the second use of the recurrent parent, "BC2" refers to the third use of the recurrent parent, and so on.

A centimorgan ("cM") is a unit of measure of recombination frequency. One cM is equal to a 1% chance that a marker at one genetic locus will be separated from a marker at a second locus due to crossing over in a single generation.

Chilling tolerance is naturally found in species from temperate or boreal zones and allows survival and an enhanced growth at low but non-freezing temperatures. Species from tropical or subtropical zones are chilling sensitive and often show wilting, chlorosis or necrosis, slowed growth and even death at temperatures around 10° C. during one or more stages of development. Accordingly, improved or enhanced "chilling tolerance" or variations thereof refers herein to improved adaptation to low but non-freezing temperatures around 15° C., preferably temperatures between 1 to 18° C., more preferably 4-14° C., and most preferred 8 to 12° C.; hereinafter called "chilling temperature".

As used herein, the term "chromosomal interval" designates a contiguous linear span of genomic DNA that resides in planta on a single chromosome. The genetic elements or genes located on a single chromosomal interval are physically linked. The size of a chromosomal interval is not particularly limited. In some aspects, the genetic elements located within a single chromosomal interval are genetically linked, typically with a genetic recombination distance of, for example, less than or equal to 20 cM, or alternatively, less than or equal to 10 cM. That is, two genetic elements within a single chromosomal interval undergo recombination at a frequency of less than or equal to 20% or 10%.

A "chromosome" is a single piece of coiled DNA containing many genes that act and move as a unity during cell division and therefore can be said to be linked. It can also be referred to as a "linkage group".

The phrase "closely linked", in the present application, means that recombination between two linked loci occurs with a frequency of equal to or less than about 10% (i.e., are separated on a genetic map by not more than 10 cM). Put another way, the closely linked loci co-segregate at least 90% of the time. Marker loci are especially useful in the present invention when they demonstrate a significant probability of co-segregation (linkage) with a desired trait. Closely linked loci such as a marker locus and a second locus can display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination a frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "proximal to" each other. In some cases, two different markers can have the same genetic map coordinates. In that case, the two markers are in such close proximity to each other that recombination occurs between them with such low frequency that it is undetectable.

The term "complement" refers to a nucleotide sequence that is complementary to a given nucleotide sequence, i.e. the sequences are related by the Watson-Crick base-pairing rules.

When referring to the relationship between two genetic elements, such as a genetic element contributing to a trait of interest and a proximal marker, "coupling" phase linkage indicates the state where the "favorable" allele at the genetic element contributing to increased resistance to anthracnose is physically associated on the same chromosome strand as the "favorable" allele of the respective linked marker locus. In coupling phase, both favorable alleles are inherited together by progeny that inherit that chromosome strand.

A plant referred to herein as "diploid" has two sets (genomes) of chromosomes.

A plant referred to herein as a "doubled haploid" is developed by doubling the haploid set of chromosomes (i.e., half the normal number of chromosomes). A doubled haploid plant has two identical sets of chromosomes, and all loci are considered homozygous.

"Elite line" means any line that has resulted from breeding and selection for superior agronomic performance. An "elite population" is an assortment of elite individuals or lines that can be used to represent the state of the art in terms of agronomically superior genotypes of a given crop species. Similarly, an "elite germplasm" or elite strain of germplasm is an agronomically superior germplasm.

A "favorable allele" is the allele at a particular locus that confers, or contributes to, an agronomically desirable phenotype, e.g., increased chilling tolerance, in a sorghum plant, and that allows the identification of plants with that agronomically desirable phenotype. A favorable allele of a marker is a marker allele that segregates with the favorable phenotype.

"Fragment" is intended to mean a portion of a nucleotide sequence. Fragments can be used as hybridization probes or PCR primers using methods disclosed herein.

A "genetic map" is a description of genetic linkage relationships among loci on one or more chromosomes (or linkage groups) within a given species, generally depicted in a diagrammatic or tabular form. For each genetic map, distances between loci are measured by how frequently their alleles appear together in a population (their recombination frequencies). Alleles can be detected using DNA or protein markers, or observable phenotypes. A genetic map is a product of the mapping population, types of markers used, and the polymorphic potential of each marker between different populations. Genetic distances between loci can differ from one genetic map to another. However, information can be correlated from one map to another using common markers. One of ordinary skill in the art can use common marker positions to identify positions of markers and other loci of interest on each individual genetic map. The order of loci should not change between maps, although frequently there are small changes in marker orders due to e.g. markers detecting alternate duplicate loci in different populations, differences in statistical approaches used to order the markers, novel mutation or laboratory error.

A "genetic map location" is a location on a genetic map relative to surrounding genetic markers on the same linkage group where a specified marker can be found within a given species.

"Genetic mapping" is the process of defining the linkage relationships of loci through the use of genetic markers, populations segregating for the markers, and standard genetic principles of recombination frequency.

"Genetic markers" are nucleic acids that are polymorphic in a population and where the alleles of which can be detected and distinguished by one or more analytic methods, e.g., RFLP, AFLP, isozyme, SNP, SSR, and the like. The term also refers to nucleic acid sequences complementary to the genomic sequences, such as nucleic acids used as probes. Markers corresponding to genetic polymorphisms between members of a population can be detected by methods well-established in the art. These include, e.g., PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also known for the detection of expressed sequence tags (ESTs) and SSR markers derived from EST sequences and randomly amplified polymorphic DNA (RAPD).

"Genetic recombination frequency" is the frequency of a crossing over event (recombination) between two genetic loci. Recombination frequency can be observed by following the segregation of markers and/or traits following meiosis.

"Genome" refers to the total DNA, or the entire set of genes, carried by a chromosome or chromosome set.

The term "genotype" is the genetic constitution of an individual (or group of individuals) at one or more genetic loci. Genotype is defined by the allele(s) of one or more known loci that the individual has inherited from its parents. The term genotype can be used to refer to an individual's genetic constitution at a single locus, at multiple loci, or, more generally, the term genotype can be used to refer to an individual's genetic make-up for all the genes in its genome.

"Germplasm" refers to genetic material of or from an individual (e.g., a plant), a group of individuals (e.g., a plant line, variety or family), or a clone derived from a line, variety, species, or culture, or more generally, all individuals within a species or for several species. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leaf, stem, pollen, or cells, which can be cultured into a whole plant.

A plant referred to as "haploid" has a single set (genome) of chromosomes.

A "haplotype" is the genotype of an individual at a plurality of genetic loci, i.e. a combination of alleles. Typically, the genetic loci described by a haplotype are physically and genetically linked, i.e., on the same chromosome segment. The term "haplotype" can refer to alleles at a particular locus, or to alleles at multiple loci along a chromosomal segment.

The term "heterogeneity" is used to indicate that individuals within the group differ in genotype at one or more specific loci.

An individual is "heterozygous" if more than one allele type is present at a given locus (e.g., a diploid individual with one copy each of two different alleles).

The term "homogeneity" indicates that members of a group have the same genotype at one or more specific loci.

An individual is "homozygous" if the individual has only one type of allele at a given locus (e.g., a diploid individual has a copy of the same allele at a locus for each of two homologous chromosomes).

The term "hybrid" refers to the progeny obtained between the crossing of at least two genetically dissimilar parents.

"Hybridization" or "nucleic acid hybridization" refers to the pairing of complementary RNA and DNA strands as well as the pairing of complementary DNA single strands.

The term "hybridize" means to form base pairs between complementary regions of nucleic acid strands.

The term "inbred" refers to a line that has been bred for genetic homogeneity.

The term "introgression" refers to the transmission of a desired allele of a genetic locus from one genetic background to another. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., detected by a marker that is associated with a phenotype, at a QTL, a transgene, or the like. In any case, offspring comprising the desired allele can be repeatedly backcrossed to a line having a desired genetic background and selected for the desired allele, to result in the allele becoming fixed in a selected genetic background.

The process of "introgressing" is often referred to as "backcrossing" when the process is repeated two or more times.

A "line" or "strain" is a group of individuals of identical parentage that are generally inbred to some degree and that are generally homozygous and homogeneous at most loci (isogenic or near isogenic). A "subline" refers to an inbred subset of descendants that are genetically distinct from other similarly inbred subsets descended from the same progenitor.

As used herein, the term "linkage" is used to describe the degree with which one marker locus is associated with another marker locus or some other locus. The linkage relationship between a molecular marker and a locus affecting a phenotype is given as a "probability" or "adjusted probability". Linkage can be expressed as a desired limit or range. For example, in some embodiments, any marker is linked (genetically and physically) to any other marker when the markers are separated by less than 50, 40, 30, 25, 20, or 15 map units (or cM). In some aspects, it is advantageous to define a bracketed range of linkage, for example, between 10 and 20 cM, between 10 and 30 cM, or between 10 and 40 cM. The more closely a marker is linked to a second locus, the better an indicator for the second locus that marker becomes. Thus, "closely linked loci" such as a marker locus and a second locus display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "in proximity to" each other. Since one cM is the distance between two markers that show a 1% recombination frequency, any marker is closely linked (genetically and physically) to any other marker that is in close proximity, e.g., at or less than 10 cM distant. Two closely linked markers on the same chromosome can be positioned 9, 8, 7, 6, 5, 4, 3, 2, 1, 0.75, 0.5 or 0.25 cM or less from each other.

The term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency. Markers that show linkage disequilibrium are considered linked. Linked loci co-segregate more than 50% of the time, e.g., from about 51% to about 100% of the time. In other words, two markers that co-segregate have a recombination frequency of less than 50% (and by definition, are separated by less than 50 cM on the same linkage group.) As used herein, linkage can be between two markers, or alternatively between a marker and a locus affecting a phenotype. A marker locus can be "associated with" (linked to) a trait. The degree of linkage of a marker locus and a locus affecting a phenotypic trait is measured, e.g., as a statistical probability of co-segregation of that molecular marker with the phenotype (e.g., an F statistic or LOD score).

Linkage disequilibrium is most commonly assessed using the measure $r^2$, which is calculated using the formula described by Hill, W. G. and Robertson, A, Theor. Appl. Genet. 38:226-231 (1968). When $r^2=1$, complete linkage disequilibrium exists between the two marker loci, meaning that the markers have not been separated by recombination and have the same allele frequency. The $r^2$ value will be dependent on the population used. Values for $r^2$ above ⅓ indicate sufficiently strong linkage disequilibrium to be useful for mapping (Ardlie et al., Nature Reviews Genetics 3:299-309 (2002)). Hence, alleles are in linkage disequilibrium when $r^2$ values between pairwise marker loci are greater than or equal to 0.33, 0.4, 0.5, 0.6, 0.7, 0.8, 0.9, or 1.0.

A "locus" is a position on a chromosome, e.g. where a nucleotide, gene, sequence, or marker is located.

The "logarithm of odds (LOD) value" or "LOD score" (Risch, Science 255:803-804 (1992)) is used in genetic interval mapping to describe the degree of linkage between two marker loci. A LOD score of three between two markers indicates that linkage is 1000 times more likely than no linkage, while a LOD score of two indicates that linkage is 100 times more likely than no linkage. LOD scores greater than or equal to two may be used to detect linkage. LOD scores can also be used to show the strength of association between marker loci and quantitative traits in "quantitative trait loci" mapping. In this case, the LOD score's size is dependent on the closeness of the marker locus to the locus affecting the quantitative trait, as well as the size of the quantitative trait effect.

A "marker" is a means of finding a position on a genetic or physical map, or else linkages among markers and trait loci (loci affecting traits). The position that the marker detects may be known via detection of polymorphic alleles and their genetic mapping, or else by hybridization, sequence match or amplification of a sequence that has been physically mapped. A marker can be a DNA marker (detects DNA polymorphisms), a protein (detects variation at an encoded polypeptide), or a simply inherited phenotype (such as the 'waxy' phenotype). A DNA marker can be developed from genomic nucleotide sequence or from expressed nucleotide sequences (e.g., from a spliced RNA or a cDNA). Depending on the DNA marker technology, the marker will consist of complementary primers flanking the locus and/or complementary probes that hybridize to polymorphic alleles at the locus. A DNA marker, or a genetic marker, can also be used to describe the gene, DNA sequence or nucleotide on the chromosome itself (rather than the components used to detect the gene or DNA sequence) and is often used when that DNA marker is associated with a particular trait in human genetics (e.g. a marker for breast cancer). The term marker locus is the locus (gene, sequence or nucleotide) that the marker detects.

Markers that detect genetic polymorphisms between members of a population are well-established in the art. Markers can be defined by the type of polymorphism that they detect and also the marker technology used to detect the polymorphism. Marker types include but are not limited to, e.g., detection of restriction fragment length polymorphisms (RFLP), detection of isozyme markers, randomly amplified polymorphic DNA (RAPD), amplified fragment length polymorphisms (AFLPs), detection of simple sequence repeats (SSRs), detection of amplified variable sequences of the plant genome, detection of self-sustained sequence replication, or detection of single nucleotide polymorphisms (SNPs). SNPs can be detected e.g. via DNA sequencing, PCR-based sequence specific amplification methods, detection of polynucleotide polymorphisms by allele specific hybridization (ASH), dynamic allele-specific hybridization (DASH), molecular beacons, microarray hybridization, oligonucleotide ligase assays, Flap endonucleases, 5' endonucleases, primer extension, single strand conformation polymorphism (SSCP) or temperature gradient gel electrophoresis (TGGE). DNA sequencing, such as the pyrosequencing technology has the advantage of being able to detect a series of linked SNP alleles that constitute a haplotype. Haplotypes tend to be more informative (detect a higher level of polymorphism) than SNPs.

A "marker allele", alternatively an "allele of a marker locus", can refer to one of a plurality of polymorphic nucleotide sequences found at a marker locus in a population.

"Marker assisted selection" (or MAS) is a process by which individual plants are selected based on marker genotypes.

A "marker haplotype" refers to a combination of alleles at a marker locus.

A "marker locus" is a specific chromosome location in the genome of a species where a specific marker can be found. A marker locus can be used to track the presence of a second linked locus, e.g., one that affects the expression of a phenotypic trait. For example, a marker locus can be used to monitor segregation of alleles at a genetically or physically linked locus.

A "marker probe" is a nucleic acid sequence or molecule that can be used to identify the presence of a marker locus, e.g., a nucleic acid probe that is complementary to a marker locus sequence, through nucleic acid hybridization. Marker probes comprising 30 or more contiguous nucleotides of the marker locus ("all or a portion" of the marker locus sequence) may be used for nucleic acid hybridization. Alternatively, in some aspects, a marker probe refers to a probe of any type that is able to distinguish (i.e., genotype) the particular allele that is present at a marker locus.

The term "molecular marker" may be used to refer to a genetic marker, as defined above, or an encoded product thereof (e.g., a protein) used as a point of reference when identifying a linked locus. A marker can be derived from genomic nucleotide sequences or from expressed nucleotide sequences (e.g., from a spliced RNA, a cDNA, etc.), or from an encoded polypeptide. The term also refers to nucleic acid sequences complementary to or flanking the marker sequences, such as nucleic acids used as probes or primer pairs capable of amplifying the marker sequence. A "molecular marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. Nucleic acids are "complementary" when they specifically hybridize in solution, e.g., according to Watson-Crick base pairing rules. Some of the markers described herein are also referred to as hybridization markers when located on an indel region, such as the non-collinear region described herein. This is because the insertion region is, by definition, a polymorphism vis a vis a plant without the insertion. Thus, the marker need only indicate whether the indel region is present or absent. Any suitable marker detection technology may be used to identify such a hybridization marker, e.g. SNP technology is used in the examples provided herein.

An allele "negatively" correlates with a trait when it is linked to it and when presence of the allele is an indicator that a desired trait or trait form will not occur in a plant comprising the allele.

"Nucleotide sequence", "polynucleotide", "nucleic acid sequence", and "nucleic acid fragment" are used interchangeably and refer to a polymer of RNA or DNA that is single or double-stranded, optionally containing synthetic, non-natural or altered nucleotide bases. A "nucleotide" is a monomeric unit from which DNA or RNA polymers are constructed, and consists of a purine or pyrimidine base, a pentose, and a phosphoric acid group. Nucleotides (usually found in their 5' monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The term "phenotype", "phenotypic trait", or "trait" can refer to the observable expression of a gene or series of genes. The phenotype can be observable to the naked eye, or by any other means of evaluation known in the art, e.g., weighing, counting, measuring (length, width, angles, etc.), microscopy, biochemical analysis, or an electromechanical assay. In some cases, a phenotype is directly controlled by a single gene or genetic locus, i.e., a "single gene trait" or a "simply inherited trait". In the absence of large levels of environmental variation, single gene traits can segregate in a population to give a "qualitative" or "discrete" distribution, i.e. the phenotype falls into discrete classes. In other cases, a phenotype is the result of several genes and can be considered a "multigenic trait" or a "complex trait". Multigenic traits segregate in a population to give a "quantitative" or "continuous" distribution, i.e. the phenotype cannot be separated into discrete classes. Both single gene and multigenic traits can be affected by the environment in which they are being expressed, but multigenic traits tend to have a larger environmental component.

A "physical map" of the genome is a map showing the linear order of identifiable landmarks (including genes, markers, etc.) on chromosome DNA. However, in contrast to genetic maps, the distances between landmarks are absolute (for example, measured in base pairs or isolated and overlapping contiguous genetic fragments) and not based on genetic recombination (that can vary in different populations).

A "plant" can be a whole plant, any part thereof, or a cell or tissue culture derived from a plant. Thus, the term "plant" can refer to any of: whole plants, plant components or organs (e.g., leaves, stems, roots, etc.), plant tissues, seeds, plant cells, and/or progeny of the same. A plant cell is a cell of a plant, taken from a plant, or derived through culture from a cell taken from a plant.

A "polymorphism" is a variation in the DNA between two or more individuals within a population. A polymorphism preferably has a frequency of at least 1% in a population. A useful polymorphism can include a single nucleotide polymorphism (SNP), a simple sequence repeat (SSR), or an insertion/deletion polymorphism, also referred to herein as an "indel".

An allele "positively" correlates with a trait when it is linked to it and when presence of the allele is an indicator that the desired trait or trait form will occur in a plant comprising the allele.

The "probability value" or "p-value" is the statistical likelihood that the particular combination of a phenotype and the presence or absence of a particular marker allele is random. Thus, the lower the probability score, the greater the likelihood that a locus and a phenotype are associated. The probability score can be affected by the proximity of the first locus (usually a marker locus) and the locus affecting the phenotype, plus the magnitude of the phenotypic effect (the change in phenotype caused by an allele substitution). In some aspects, the probability score is considered "significant" or "nonsignificant". In some embodiments, a probability score of 0.05 (p=0.05, or a 5% probability) of random assortment is considered a significant indication of association. However, an acceptable probability can be any probability of less than 50% (p=0.5). For example, a significant probability can be less than 0.25, less than 0.20, less than 0.15, less than 0.1, less than 0.05, less than 0.01, or less than 0.001.

A "production marker" or "production SNP marker" is a marker that has been developed for high-throughput purposes. Production SNP markers are developed to detect specific polymorphisms and are designed for use with a variety of chemistries and platforms.

The term "progeny" refers to the offspring generated from a cross. A "progeny plant" is a plant generated from a cross between two plants.

The term "quantitative trait locus" or "QTL" refers to a region of DNA that is associated with the differential expression of a quantitative phenotypic trait in at least one genetic background, e.g., in at least one breeding population. The region of the QTL encompasses or is closely linked to the gene or genes that affect the trait in question. An "allele of a QTL" can comprise multiple genes or other genetic factors within a contiguous genomic region or linkage group, such as a haplotype. An allele of a QTL can denote a haplotype within a specified window wherein said window is a contiguous genomic region that can be defined, and tracked, with a set of one or more polymorphic markers. A haplotype can be defined by the unique fingerprint of alleles at each marker within the specified window.

A "reference sequence" or a "consensus sequence" is a defined sequence used as a basis for sequence comparison. The reference sequence for a PHM marker is obtained by sequencing a number of lines at the locus, aligning the nucleotide sequences in a sequence alignment program (e.g. Sequencher), and then obtaining the most common nucleotide sequence of the alignment. Polymorphisms found among the individual sequences are annotated within the consensus sequence. A reference sequence is not usually an exact copy of any individual DNA sequence, but represents an amalgam of available sequences and is useful for designing primers and probes to polymorphisms within the sequence.

In "repulsion" phase linkage, the "favorable" allele at the locus of interest is physically linked with an "unfavorable" allele at the proximal marker locus, and the two "favorable" alleles are not inherited together (i.e., the two loci are "out of phase" with each other).

The term "short stature" refers to a plant less than or equal to about 2 meters in height at maturity. The term "tall stature" refers to a plant greater than about 2 meters in height at maturity.

Sorghum is a genus of numerous species of grasses, some of which are raised for grain and many of which are used as fodder plants either cultivated or as part of pasture. Sorghum is in the subfamily Panicoideae and the tribe Andropogoneae. Sorghum is well adapted to growth in hot, arid or semi-arid areas. The many subspecies are divided into four groups: grain sorghums (such as milo), grass sorghum (for pasture and hay), sweet sorghum (used to produce sorghum syrups), and broom corn (for brooms and brushes). The name sweet sorghum is used to identify varieties of *Sorghum bicolor* that are sweet and juicy. High biomass sorghum can be used as a source of biofuels.

Sorghum species encompassed in this disclosure include, but are not limited to, *Sorghum almum, Sorghum amplum, Sorghum angustum, Sorghum arundinaceum, Sorghum bicolor* (primary cultivated species), *Sorghum brachypodum, Sorghum bulbosum, Sorghum burmahicum, Sorghum controversum, Sorghum* x *drummondii, Sorghum ecarinatum, Sorghum exstans, Sorghum grande, Sorghum halepense, Sorghum interjectum, Sorghum intrans, Sorghum laxiflorum, Sorghum leiocladum, Sorghum macrospermum, Sorghum matarankense, Sorghum miliaceum, Sorghum nigrum, Sorghum nitidum, Sorghum plumosum, Sorghum propinquum, Sorghum purpureosericeum, Sorghum stipoideum, Sorghum timorense, Sorghum trichocladum, Sorghum versicolor, Sorghum virgatum,* and *Sorghum vulgare.*

The term "sorghum plant" includes whole sorghum plants, sorghum plant cells, sorghum plant protoplast, sorghum plant cell or sorghum tissue culture from which sorghum plants can be regenerated, sorghum plant calli, sorghum plant clumps and sorghum plant cells that are intact in sorghum plants or parts of sorghum plants, such as sorghum seeds, sorghum flowers, sorghum cotyledons, sorghum leaves, sorghum stems, sorghum buds, sorghum roots, sorghum root tips and the like.

A "topcross test" is a test performed by crossing each individual (e.g. a selection, inbred line, clone or progeny individual) with the same pollen parent or "tester", usually a homozygous line.

The phrase "under stringent conditions" refers to conditions under which a probe or polynucleotide will hybridize to a specific nucleic acid sequence, typically in a complex mixture of nucleic acids, but to essentially no other sequences. Stringent conditions are sequence-dependent and will be different in different circumstances. Longer sequences hybridize specifically at higher temperatures. Generally, stringent conditions are selected to be about 5-10° C. lower than the thermal melting point (Tm) for the specific sequence at a defined ionic strength pH. The Tm is the temperature (under defined ionic strength, pH, and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3, and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions are often: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C., depending on primer length. Additional guidelines for determining hybridization parameters are provided in numerous references.

An "unfavorable allele" of a marker is a marker allele that segregates with the unfavorable plant phenotype, therefore providing the benefit of identifying plants that can be removed from a breeding program or planting.

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory Press: Cold Spring Harbor, 1989.

Chilling Tolerance in Sorghum

Previous conventional breeding efforts relied upon selecting plants based on their phenotypic appearance at seedling stage and maturity. However, linkage of chilling tolerance loci with genes providing tall stature and grain tannins, traits undesirable for US grain sorghum, stymied these conventional breeding efforts. Further complicating the conventional breeding for chilling tolerance is the lack of uniformity in chilling stress between locations and years. Therefore, the molecular markers developed allows for the tracking of seedlings containing favorable chilling tolerance loci in a segregating population and for the utilization of these plants in backcrossing to precisely introgress chilling tolerance into elite sorghum lines.

By developing early-season chilling tolerance in commercial US grain sorghum hybrids, farmers can plant sorghum by the end of April or in the first week of May when soil moisture is more abundant. Early planting of sorghum can avoid post-flowering drought stress that reduces sorghum yields drastically. In addition to grain sorghums, these molecular markers can be used to increase the chilling tolerance of forage sorghum. Early planting of forage sorghums can maximize yield by allowing multiple ratoons as the growing season is extended.

Genetic Mapping

It has been recognized for quite some time that specific genetic loci correlating with particular traits can be mapped in an organism's genome. The plant breeder can advantageously use molecular markers to identify desired individuals by detecting marker alleles that show a statistically significant probability of co-segregation with a desired phenotype, manifested as linkage disequilibrium. By identifying a molecular marker or clusters of molecular markers that co-segregate with a trait of interest, the breeder is able to rapidly select a desired phenotype by selecting for the proper molecular marker allele (a process called marker-assisted selection).

A variety of methods well known in the art are available for detecting molecular markers or clusters of molecular markers that co-segregate with a trait of interest, such as chilling tolerance in sorghum. The basic idea underlying these methods is the detection of markers, for which alternative genotypes (or alleles) have significantly different average phenotypes. Thus, one makes a comparison among marker loci of the magnitude of difference among alternative genotypes (or alleles) or the level of significance of that difference. Trait genes are inferred to be located nearest the marker(s) that have the greatest associated genotypic difference. Two such methods used to detect trait loci of interest are: 1) Population-based association analysis and 2) Traditional linkage analysis.

In a population-based association analysis, lines are obtained from pre-existing populations with multiple founders, e.g. elite breeding lines. Population-based association analyses rely on linkage disequilibrium (LD) and the idea that in an unstructured population, only correlations between genes controlling a trait of interest and markers closely linked to those genes will remain after so many generations of random mating. In reality, most pre-existing populations have population substructure. Thus, the use of a structured association approach helps to control population structure by allocating individuals to populations using data obtained from markers randomly distributed across the genome, thereby minimizing disequilibrium due to population structure within the individual populations (also called subpopulations). The phenotypic values are compared to the genotypes (alleles) at each marker locus for each line in the subpopulation. A significant marker-trait association indicates the close proximity between the marker locus and one or more genetic loci that are involved in the expression of that trait.

The same principles underlie traditional linkage analysis; however, linkage disequilibrium is generated by creating a population from a small number of founders. The founders are selected to maximize the level of polymorphism within the constructed population, and polymorphic sites are assessed for their level of cosegregation with a given phenotype. A number of statistical methods have been used to identify significant marker-trait associations. One such method is an interval mapping approach (Lander and Botstein, Genetics 121:185-199 (1989), in which each of many positions along a genetic map (say at 1 cM intervals) is tested for the likelihood that a gene controlling a trait of interest is located at that position. The genotype/phenotype data are used to calculate for each test position a LOD score (log of likelihood ratio). When the LOD score exceeds a threshold value, there is significant evidence for the location of a gene controlling the trait of interest at that position on the genetic map (which will fall between two particular marker loci).

The present invention provides sorghum marker loci that demonstrate statistically significant co-segregation with chilling tolerance as determined by traditional linkage analysis. Detection of these loci or additional linked loci can be used in marker assisted sorghum breeding programs to produce plants with increased chilling tolerance.

QTL Locations

QTL on chromosomes 1, 2, 4, 5, 7, and 9 were identified as being associated with chilling tolerance (Example 1, Table 5). QTL for one or more seedling traits that mapped within a 2 Mb interval were assigned a common name. qSbCT01.06 describes a QTL on chromosome 1 close to 6 Mb, qSbCT01.13 describes a QTL on chromosome 1 close to 13 Mb, qSbCT01.57 describes a QTL on chromosome 1 close to 57 Mb, qSbCT02.08 describes a QTL on chromosome 2 close to 8 Mb, qSbCT04.62 describes a QTL on chromosome 4 close to 62 Mb, qSbCT05.04 describes a QTL on chromosome 5 close to 4 Mb, qSbCT07.10 describes a QTL on chromosome 7 close to 10 Mb, qSbCT07.59 describes a QTL on chromosome 7 close to 59 Mb, and qSbCT09.57 describes a QTL on chromosome 9 close to 57 Mb.

Chromosomal Intervals

Chromosomal intervals that correlate with chilling tolerance in sorghum and other related cereal plants are provided. A variety of methods well known in the art are available for identifying chromosomal intervals. The boundaries of such chromosomal intervals are drawn to encompass markers that will be linked to the gene(s) controlling the trait of interest. In other words, the chromosomal interval is drawn such that any marker that lies within that interval (including the terminal markers that define the boundaries of the interval) can be used as a marker for chilling tolerance.

Each interval comprises at least one QTL, and furthermore, may indeed comprise more than one QTL. Close proximity of multiple QTL in the same interval may obfuscate the correlation of a particular marker with a particular QTL, as one marker may demonstrate linkage to more than one QTL. Conversely, e.g., if two markers in close proximity show co-segregation with the desired phenotypic trait, it is sometimes unclear if each of those markers identifies the same QTL or two different QTL. Regardless, knowledge of how many QTL are in a particular interval is not necessary to make or practice the invention.

The intervals described encompass markers that co-segregate with chilling tolerance in a number of populations. The clustering of markers that co-segregate with a trait within a localized region occurs in relatively small domains on the chromosomes, indicating the presence of one or more QTL in those chromosome regions. The interval was drawn to encompass markers that co-segregate with chilling tolerance (as well as the other related traits). Any marker located within the intervals can find use as a marker for chilling tolerance and can be used in the context of the methods presented herein to identify and/or select sorghum plants that have increased chilling tolerance.

The qSbCT01.06 interval may encompass any of the markers identified herein as being associated with chilling tolerance including S1_5730743 and S1_6902771. The qSbCT01.13 interval may encompass any of the markers identified herein as being associated with chilling tolerance including S1_9756192, S1_13188261, and S1_13526795. The qSbCT01.57 interval may encompass any of the markers identified herein as being associated with chilling tolerance including S1_57941435. The qSbCT02.08 interval may encompass any of the markers identified herein as being associated with chilling tolerance including S2_8672301, S2_9218398, and S2_9260382. The qSbCT04.62 interval may encompass any of the markers identified herein as being associated with chilling tolerance including S4_62368531 and S4_62455479. The qSbCT05.04 interval may encompass any of the markers identified herein as being associated with chilling tolerance including S5_4284787 and S5_4403613. The qSbCT07.10 interval may encompass any of the markers identified herein as being associated with chilling tolerance including S7_8916696 and S7_12580350. The qSbCT07.59 interval may encompass any of the markers identified herein as being associated with chilling tolerance including S7_59290017 and S7_59915577. The qSbCT09.57 interval may encompass any of the markers identified herein as being associated with chilling tolerance including S9_55625332 and S9_58070153.

Chromosomal intervals can also be defined by markers that are linked to (show linkage disequilibrium with) a QTL marker and $r^2$ is a common measure of linkage disequilibrium in the context of association studies.

Markers and Linkage Relationships

A common measure of linkage is the frequency with which traits cosegregate. This can be expressed as a percentage of cosegregation (recombination frequency) or in centiMorgans (cM). The cM is a unit of measure of genetic recombination frequency. One cM is equal to a 1% chance that a trait at one genetic locus will be separated from a trait at another locus due to crossing over in a single generation (meaning the traits segregate together 99% of the time). Because chromosomal distance is approximately proportional to the frequency of crossing over events between traits, there is an approximate physical distance that correlates with recombination frequency.

Marker loci are themselves traits and can be assessed according to standard linkage analysis by tracking the marker loci during segregation. Thus, one cM is equal to a 1% chance that a marker locus will be separated from another locus, due to crossing over in a single generation.

The closer a marker is to a gene controlling a trait of interest, the more effective and advantageous that marker is as an indicator for the desired trait. Closely linked loci display an inter-locus cross-over frequency of about 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci (e.g., a marker locus and a target locus) display a recombination frequency of about 1% or less, e.g., about 0.75% or less, more preferably about 0.5% or less, or yet more preferably about 0.25% or less. Thus, the loci are about 10 cM, 9 cM, 8 cM, 7 cM, 6 cM, 5 cM, 4 cM, 3 cM, 2 cM, 1 cM, 0.75 cM, 0.5 cM or 0.25 cM or less apart. Put another way, two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are said to be "proximal to" each other.

Although particular marker alleles can co-segregate with increased or decreased chilling tolerance, it is important to note that the marker locus is not necessarily responsible for the expression of the chilling tolerance phenotype. For example, it is not a requirement that the marker polynucleotide sequence be part of a gene that is responsible for the phenotype (for example, is part of the gene open reading frame). The association between a specific marker allele and a trait is due to the original "coupling" linkage phase between the marker allele and the allele in the ancestral sorghum line from which the allele originated. Eventually, with repeated recombination, crossing over events between the marker and genetic locus can change this orientation. For this reason, the favorable marker allele may change depending on the linkage phase that exists within the parent having the favorable trait that is used to create segregating populations. This does not change the fact that the marker can be used to monitor segregation of the phenotype. It only changes which marker allele is considered favorable in a given segregating population.

Methods presented herein include detecting the presence of one or more marker alleles associated with increased chilling tolerance in a sorghum plant and then identifying and/or selecting sorghum plants that have favorable alleles at those marker loci, or detecting the presence of a marker allele associated with decreased chilling tolerance and then identifying and/or counterselecting sorghum plants that have unfavorable alleles. Markers have been identified herein as being associated with chilling tolerance in sorghum and hence can be used to identify and select sorghum plants having increased chilling tolerance. Any marker within 20 cM, 15 cM, 10 cM, 9 cM, 8 cM, 7 cM, 6 cM, 5 cM, 4 cM, 3 cM, 2 cM, 1 cM, 0.9 cM, 0.8 cM, 0.7 cM, 0.6 cM, 0.5 cM, 0.4 cM, 0.3 cM, 0.2 cM, 0.1 cM or less of any of the markers identified herein could also be used to identify and select sorghum plants with increased chilling tolerance. Any marker allele linked to and associated with the favorable alleles of the markers listed herein can be used for detection purposes in the identification and/or selection of plants with increased chilling tolerance.

Marker Assisted Selection

Molecular markers can be used in a variety of plant breeding applications (e.g. see Staub et al. (1996) Hortscience 31:729-741; Tanksley (1983) Plant Molecular Biology Reporter. 1:3-8). One of the main areas of interest is to increase the efficiency of backcrossing and introgressing genes using marker-assisted selection. A molecular marker that demonstrates linkage with a locus affecting a desired phenotypic trait provides a useful tool for the selection of the trait in a plant population. This is particularly true where the phenotype is hard to assay. Since DNA marker assays are less laborious and take up less physical space than field phenotyping, much larger populations can be assayed, increasing the chances of finding a recombinant with the target segment from the donor line moved to the recipient line. The closer the linkage, the more useful the marker, as recombination is less likely to occur between the marker and the gene causing the trait, which can result in false positives. Having flanking markers decreases the chances that false positive selection will occur as a double recombination event would be needed. The ideal situation is to have a marker in the gene itself, so that recombination cannot occur between the marker and the gene. Such a marker is called a 'perfect marker'.

When a gene is introgressed by marker assisted selection, it is not only the gene that is introduced but also the flanking regions (Gepts. (2002). Crop Sci; 42:1780-1790). This is referred to as "linkage drag." In the case where the donor plant is highly unrelated to the recipient plant, these flanking regions carry additional genes that may code for agronomically undesirable traits. This "linkage drag" may also result in reduced yield or other negative agronomic characteristics even after multiple cycles of backcrossing into the elite sorghum line. This is also sometimes referred to as "yield drag." The size of the flanking region can be decreased by additional backcrossing, although this is not always successful, as breeders do not have control over the size of the region or the recombination breakpoints (Young et al. (1998) Genetics 120:579-585). In classical breeding it is usually only by chance that recombinations are selected that contribute to a reduction in the size of the donor segment (Tanksley et al. (1989). Biotechnology 7:257-264). Even after 20 backcrosses in backcrosses of this type, one may expect to find a sizeable piece of the donor chromosome still linked to the gene being selected. With markers however, it is possible to select those rare individuals that have experienced recombination near the gene of interest. In 150 backcross plants, there is a 95% chance that at least one plant will have experienced a crossover within 1 cM of the gene. Markers will allow unequivocal identification of those individuals. With one additional backcross of 300 plants, there would be a 95% chance of a crossover within 1 cM of the other side of the gene, generating a segment around the target gene of less than 2 cM. This can be accomplished in two generations with markers, while it would have required on average 100 generations without markers (See Tanksley et al., supra). When the exact location of a gene is known, flanking markers surrounding the gene can be utilized to select for recombinations in different population sizes. For example, in smaller population sizes, recombinations may be expected further away from the gene, so more distal flanking markers would be required to detect the recombination.

The key components to the implementation of marker assisted selection are: (i) Defining the population within which the marker-trait association will be determined, which can be a segregating population, or a random or structured population; (ii) monitoring the segregation or association of polymorphic markers relative to the trait, and determining linkage or association using statistical methods; (iii) defining a set of desirable markers based on the results of the statistical analysis, and (iv) the use and/or extrapolation of this information to the current set of breeding germ plasm to enable marker-based selection decisions to be made. The markers described in this disclosure, as well as other marker types such as SSRs and FLPs, can be used in marker assisted selection protocols.

SSRs can be defined as relatively short runs of tandemly repeated DNA with lengths of 6 bp or less (Tautz (1989) Nucleic Acid Research 17:6463-6471; Wang et al. (1994) Theoretical and Applied Genetics, 88:1-6). Polymorphisms arise due to variation in the number of repeat units, probably caused by slippage during DNA replication (Levinson and Gutman (1987) Mol Biol Evol 4:203-221). The variation in repeat length may be detected by designing PCR primers to the conserved non-repetitive flanking regions (Weber and May (1989) Am J Hum Genet. 44:388-396). SSRs are highly suited to mapping and marker assisted selection as they are multi-allelic, codominant, reproducible and amenable to high throughput automation (Rafalski et al. (1996) Generating and using DNA markers in plants. In: Non-mammalian genomic analysis: a practical guide. Academic press. pp 75-135).

Various types of SSR markers can be generated, and SSR profiles can be obtained by gel electrophoresis of the amplification products. Scoring of marker genotype is based on the size of the amplified fragment. Various types of FLP markers can also be generated. Most commonly, amplification primers are used to generate fragment length polymorphisms. Such FLP markers are in many ways similar to SSR markers, except that the region amplified by the primers is not typically a highly repetitive region. Still, the amplified region, or amplicon, will have sufficient variability among germplasm, often due to insertions or deletions, such that the fragments generated by the amplification primers can be distinguished among polymorphic individuals, and such indels are known to occur frequently in sorghum (Evans et al. PLos One (2013). 8 (11): e79192).

SNP markers detect single base pair nucleotide substitutions. Of all the molecular marker types, SNPs are the most abundant, thus having the potential to provide the highest genetic map resolution (PLos One (2013). 8 (11): e79192). SNPs can be assayed at an even higher level of throughput than SSRs, in a so-called 'ultra-high-throughput' fashion, as they do not require large amounts of DNA and automation of the assay may be straight-forward. SNPs also have the promise of being relatively low-cost systems. These three factors together make SNPs highly attractive for use in marker assisted selection. Several methods are available for SNP genotyping, including but not limited to, hybridization, primer extension, oligonucleotide ligation, nuclease cleavage, minisequencing and coded spheres. Such methods have been reviewed in: Gut (2001) Hum Mutat 17 pp. 475-492; Shi (2001) Clin Chem 47, pp. 164-172; Kwok (2000) Pharmacogenomics 1, pp. 95-100; and Bhattramakki and Rafalski (2001) Discovery and application of single nucleotide polymorphism markers in plants. In: R. J. Henry, Ed, Plant Genotyping: The DNA Fingerprinting of Plants, CABI Publishing, Wallingford. A wide range of commercially available technologies utilize these and other methods to interrogate SNPs including MASSCODE™ (Qiagen) cleavable mass spectrometry tags, INVADER®. (Third Wave Technologies) and INVADER PLUS® invasive cleavage-based signal amplification, SNAPSHOT®. (Applied Biosystems) primer extension assays, TAQMAN®. (Applied Biosystems) probe-based real-time PCR assays, and BEADARRAY®. (Illumina) bead-based microarray technologies.

A number of SNPs together within a sequence, or across linked sequences, can be used to describe a haplotype for any particular genotype (Ching et al. (2002), BMC Genet. 3:19 pp Gupta et al. 2001, Rafalski (2002b), Plant Science 162:329-333). Haplotypes can be more informative than single SNPs and can be more descriptive of any particular genotype. For example, a single SNP may be allele 'T' for a specific line or variety with early maturity, but the allele 'T' might also occur in the sorghum breeding population being utilized for recurrent parents. In this case, a haplotype, e.g. a combination of alleles at linked SNP markers, may be more informative. Once a unique haplotype has been assigned to a donor chromosomal region, that haplotype can be used in that population or any subset thereof to determine whether an individual has a particular gene. See, for example, WO2003054229. Using automated high throughput marker detection platforms known to those of ordinary skill in the art makes this process highly efficient and effective.

In addition to SSR's, FLPs and SNPs, as described above, other types of molecular markers are also widely used, including but not limited to expressed sequence tags (ESTs), SSR markers derived from EST sequences, randomly amplified polymorphic DNA (RAPD), and other nucleic acid based markers.

Isozyme profiles and linked morphological characteristics can, in some cases, also be indirectly used as markers. Even though they do not directly detect DNA differences, they are often influenced by specific genetic differences. However, markers that detect DNA variation are far more numerous and polymorphic than isozyme or morphological markers (Tanksley (1983) Plant Molecular Biology Reporter 1:3-8).

Sequence alignments or contigs may also be used to find sequences upstream or downstream of the specific markers listed herein. These new sequences, close to the markers described herein, are then used to discover and develop functionally equivalent markers. For example, different physical and/or genetic maps are aligned to locate equivalent markers not described within this disclosure but that are within similar regions. These maps may be within the sorghum species, or even across other species that have been genetically or physically aligned with sorghum, such as maize, rice, wheat, or barley.

In general, marker assisted selection uses polymorphic markers that have been identified as having a significant likelihood of co-segregation with a phenotype, such as chilling tolerance in sorghum. Such markers are presumed to map near a gene or genes that regulate chilling tolerance in a sorghum plant, and are considered indicators for the desired trait, or markers. Plants are tested for the presence of a desired allele in the marker, and plants containing a desired genotype at one or more loci are expected to transfer the desired genotype, along with a desired phenotype, to their progeny. Thus, sorghum plants with increased chilling tolerance can be selected for by detecting one or more marker alleles, and in addition, progeny plants derived from those plants can also be selected. Hence, a plant containing a desired genotype in a given chromosomal region is obtained and then crossed to another plant. The progeny of such a cross would then be evaluated genotypically using one or more markers and the progeny plants with the same genotype in a given chromosomal region would then be selected as exhibiting increased chilling tolerance.

Markers were identified from linkage mapping analysis as being associated with chilling tolerance. The SNPs identified herein could be used alone or in combination (i.e. a SNP haplotype) to select for plants having a favorable QTL allele (i.e. associated with increased chilling tolerance). The skilled artisan would expect that there might be additional polymorphic sites at marker loci in and around the markers identified herein, wherein one or more polymorphic sites is in linkage disequilibrium with an allele at one or more of the polymorphic sites in the haplotype and thus could be used in a marker assisted selection program to introgress a QTL allele of interest. Two particular alleles at different polymorphic sites are said to be in linkage disequilibrium if the presence of the allele at one of the sites tends to predict the presence of the allele at the other site on the same chromosome (Stevens, Mol. Diag. 4:309-17 (1999)).

The skilled artisan would understand that allelic frequency (and hence, haplotype frequency) can differ from one germplasm pool to another. Germplasm pools vary due to maturity differences, heterotic groupings, geographical distribution, etc. As a result, SNPs and other polymorphisms may not be informative in some germplasm pools.

Use in Breeding Methods

The plants of the disclosure may be used in a plant breeding program. The goal of plant breeding is to combine, in a single variety or hybrid, various desirable traits. For field crops, these traits may include, for example, resistance to diseases and insects, tolerance to heat and drought, tolerance to chilling or freezing, reduced time to crop maturity, greater yield and better agronomic quality. With mechanical harvesting of many crops, uniformity of plant characteristics such as germination and stand establishment, growth rate, maturity and plant and ear height is desirable.

Traditional plant breeding is an important tool in developing new and improved commercial crops. This disclosure encompasses methods for producing a plant by crossing a first parent plant with a second parent plant wherein one or both of the parent plants is a plant displaying a phenotype as described herein.

Plant breeding techniques known in the art and used in a plant breeding program include, but are not limited to, recurrent selection, bulk selection, mass selection, back-crossing, pedigree breeding, open pollination breeding, restriction fragment length polymorphism enhanced selection, genetic marker enhanced selection, doubled haploids and transformation. Often combinations of these techniques are used.

The development of hybrids in a plant breeding program requires, in general, the development of homozygous inbred lines, the crossing of these lines and the evaluation of the crosses. There are many analytical methods available to evaluate the result of a cross. The oldest and most traditional method of analysis is the observation of phenotypic traits. Alternatively, the genotype of a plant can be examined.

A genetic trait which has been engineered into a particular plant using transformation techniques can be moved into another line using traditional breeding techniques that are well known in the plant breeding arts. For example, a backcrossing approach is commonly used to move a transgene from a transformed plant to an elite inbred line and the resulting progeny would then comprise the transgene(s). Also, if an inbred line was used for the transformation, then the transgenic plants could be crossed to a different inbred in order to produce a transgenic hybrid plant. As used herein, "crossing" can refer to a simple X by Y cross or the process of backcrossing, depending on the context.

The development of a hybrid in a plant breeding program involves three steps: (1) the selection of plants from various germplasm pools for initial breeding crosses; (2) the selfing of the selected plants from the breeding crosses for several generations to produce a series of inbred lines, which, while different from each other, breed true and are highly homozygous and (3) crossing the selected inbred lines with different inbred lines to produce the hybrids. During the inbreeding process, the vigor of the lines decreases. Vigor is restored when two different inbred lines are crossed to produce the hybrid. An important consequence of the homozygosity and homogeneity of the inbred lines is that the hybrid created by crossing a defined pair of inbreds will always be the same. Once the inbreds that give a superior hybrid have been identified, the hybrid seed can be reproduced indefinitely as long as the homogeneity of the inbred parents is maintained.

Plants of the present disclosure may be used to produce, e.g., a single cross hybrid, a three-way hybrid or a double cross hybrid. A single cross hybrid is produced when two inbred lines are crossed to produce the F1 progeny. A double cross hybrid is produced from four inbred lines crossed in pairs (A×B and C×D) and then the two F1 hybrids are crossed again (A×B) times (C×D). A three-way cross hybrid is produced from three inbred lines where two of the inbred lines are crossed (A×B) and then the resulting F1 hybrid is crossed with the third inbred (A×B)×C. Much of the hybrid vigor and uniformity exhibited by F1 hybrids is lost in the next generation (F2). Consequently, seed produced by hybrids is consumed rather than planted.

This invention can be better understood by reference to the following non-limiting examples. It will be appreciated by those skilled in the art that other embodiments of the invention may be practiced without departing from the spirit and the scope of the invention as herein disclosed and claimed.

EXAMPLES

Example 1: Genetic Architecture of Chilling Tolerance in Sorghum Dissected with a Nested Association Mapping Population Development of NAM Population for Chilling Tolerance Studies The chilling NAM population consists of three biparental populations that share a common parent, the US reference line BTx623. The NAM founders were selected based on their contrasting chilling responses from early planting in preliminary studies in Lubbock, Texas. Chilling-sensitive BTx623 was used as the seed parent in crosses with three chilling-tolerant Chinese founders, Niu Sheng Zui (NSZ; PI 568016), Hong Ke Zi (HKZ; PI 567946), and Kaoliang (Kao; PI 562744) in Lubbock, Texas. BTx623 is derived from Combine Kafir×SC170, an Ethiopian zerazera cauda-tum. The resulting $F_1$ progenies were self-pollinated to generate three segregating $F_2$ populations. RILs were developed using single-seed descent by selfing to the $F_6$ generation in Lubbock, Texas (summer nursery) and Guayanilla, Puerto Rico (winter nursery). The $F_{6:7}$ RILs were derived by combining seeds of 3-4 uniform panicles. Additional seed increase of the NAM population was conducted in Puerto Vallarta, Mexico (winter nursery), by selfing the $F_{6:7}$ plants to derive $F_{6:8}$ RILs. Below, the Chinese founder name will be used when referring to a given RIL family (e.g., the NSZ family). The resulting chilling NAM population (n=771) comprised 293, 256, and 222 RILs for the NSZ, Kao, and HKZ families, respectively.

Early- and Normal-Planted Field Trials

Six early- and two normal-planted field trials were conducted in 2016, 2017, and 2018 in Kansas (Table 1). Three locations, two in eastern Kansas [Ashland Bottoms (AB), 39.14N-96.63W; Manhattan (MN), 39.21N-96.60W] and one in western Kansas [Agricultural Research Center, Hays (HA), 38.86N-99.33W], were used for field trials (FIG. 1A). Abbreviated location name and the last two digits of the year (e.g. AB16 for Ashland Bottoms 2016) were assigned for each field trial. A suffix was added to the AB16 field trials, AB16_b1 and AB16_b2, as both were planted in AB with an interval of two weeks between plantings. The $F_{6:7}$ RILs were planted in AB16, while $F_{6:8}$ RILs were planted in AB, MN, and HA in 2017 and 2018. Each field trial contained two replicates of the NAM population. The NAM RILs were randomized within family in 2016, and completely randomized in 2017 and 2018 in each replicate block (FIGS. 1A and S2). Controls in each field trial comprised chilling-tolerant Chinese accessions NSZ, HKZ, Kao, and Shan Qui Red (SQR; PI 656025), chilling-sensitive inbreds BTx623 and RTx430, and US commercial grain sorghum hybrid Pioneer 84G62.

Five early-planted (EP, natural chilling stress) trials were sown in April and one in early May (MN17), 30-45 days earlier than normal sorghum planting in Kansas. The EP trials, except MN17, experienced chilling stress) (<15° during emergence (Table 1). Optimal temperatures) (>15° prevailed in MN17 during emergence, but one-week-old seedlings experienced chilling stress) (5-13°. Normal-planted (NP, optimal temperature) field trial was sown in June when the soil temperatures were optimal for sorghum cultivation) (>15°. AB18 was considered as the second NP trial, although planted in early May, as optimal conditions prevailed during emergence and seedling growth.

TABLE 1

Phenotyping information for early- and normal-planted field trials.

| Phenotype | AB16_b1[a] | AB16_b2[a] | AB17[a] | MN17[a] | HA17[a] | HA18[a] | AB185[b] | MN18[b] |
|---|---|---|---|---|---|---|---|---|
| Planting | Early | Early | Early | Early | Early | Early | Normal | Normal |
| Chilling Stress | Yes | Yes | Yes | Yes | Yes | Yes | No | No |
| Planting Date | April 7 | April 15 | April 25 | May 8 | April 20 | April 17 | May 7 | June 5 |
| First Emergence | April 26 | April 28 | May 8 | May 14 | May 8 | May 2 | May 10 | June 11 |
| Emergence Count | April 28 | May 2 | May 15 | May 17 | May 12 | May 10 | May 14 | June 19 |
| Seedling Vigor1 | May 10 | May 9 | May 18 | May 24 | May 16 | May 17 | — | June 19 |
| Damage Rating | May 6 | — | — | May 26 | May 23 | — | — | — |
| Seedling Vigor2 | May 19 | May 23 | May 25 | June 5 | June 6 | May 25 | May 23 | June 26 |
| Seedling Vigor3 | May 25 | May 26 | June 7 | June 9 | May 31 | June 8 | June 6 | — |

[a]Early-planted field trials, represented using a two digit field location name (in Kansas) and last two digits of the year the field trial was conducted. Field locations: Ashland Bottoms (AB), Manhattan (MN), and Hays (HA).
[b]Normal-planted field trials conducted in 2018 at AB and MN.

Our chilling tolerance studies of the NAM founders and RILs were based on natural chilling events in field trials sown 30-45 days earlier than normal. In early-planted field trial (FIGS. 1A-B) the Chinese founders had significantly greater emergence and seedling vigor (P<0.05) than BTx623 (FIGS. 1C, 1D). By contrast, no difference was observed in emergence (NPEC) between the founders under normal-planting. Chinese founder lines were much taller (~3 m) at maturity than BTx623 (1.2 m) (FIG. 1E), but little variation was observed for flowering time among the founder lines (4-5 d; P<0.05; FIG. 1F). Grain tannins were present in the Chinese accessions and absent in BTx623 (FIG. 1G).

Genetic Properties of the Chilling NAM Population

Figure 2B:
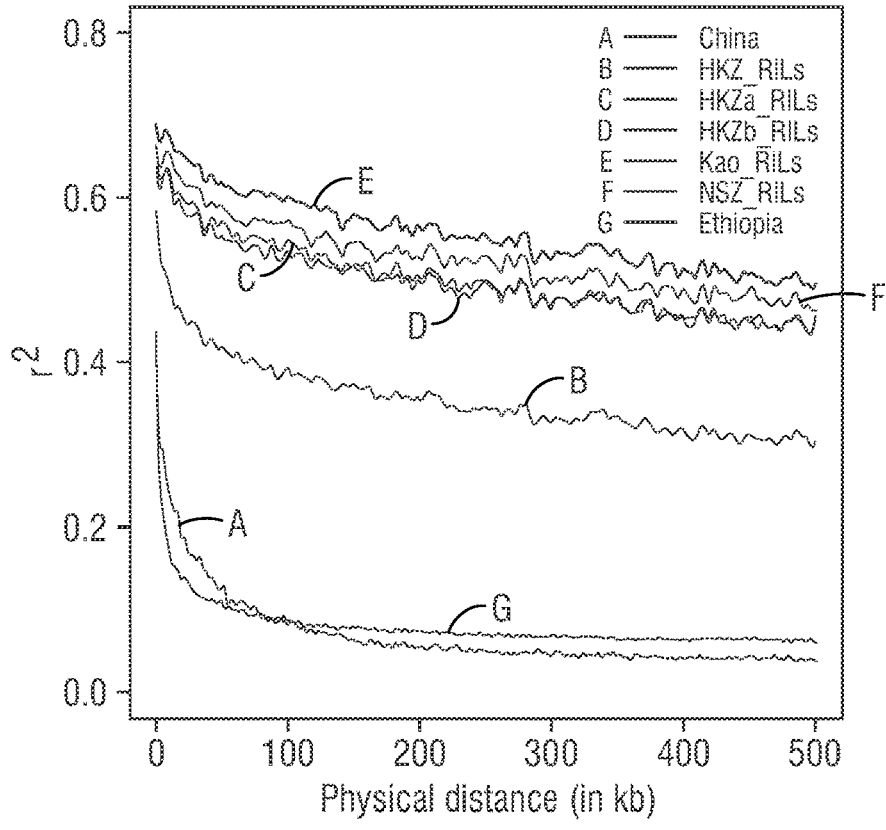

The filtered GBS data set for the chilling NAM population comprised genotypes at 43,320 SNPs. SNP densities were higher in telomeres than pericentromeric regions. To check the population's quality and understand its genetic structure, NAM RILs and founders were projected onto PCA axes built from a global sorghum diversity panel (FIG. 2A), which reflect geographic origin and botanical race. As expected, the Chinese founders clustered with durra sorghums of Asia and East Africa, while BTx623 was positioned midway between kafir and caudatum clusters, consistent with its pedigree (FIG. 2A). The three half-sib families of the chilling NAM population were clustered together, midway between the Chinese founders and BTx623. NJ analysis and PCA of the chilling NAM population by itself confirmed the expected family structure for NSZ and Kao, with each family forming a single cluster. Two clusters were observed for the HKZ family. We assigned HKZ RILs into HKZa ($n_{RIL}$=121) or HKZb ($n_{RIL}$=101) subfamilies, with the HKZb subfamily representing the cluster with PC1>40 (and the longer branch on NJ dendrogram). The LD rate decay (to genome-wide background) was slower in NAM families (~500 kb) compared to diverse accessions from China and Ethiopia (~20 kb) (FIG. 2B).

Repeatability and Heritability of Field Phenotypes

RILs were scored for emergence and seedling vigor under early- and normal-planted field trials. Early (EPSV1) and later (EPSV2, EPSV3) seedling vigor ratings were strongly correlated (0.7-0.8), as were ratings made by different individuals on the same day (0.7-0.8). By contrast, the correlation across RILs between early- and normal-planted seedling traits was low (0.1-0.3). Broad sense heritability (H2) across locations and years for early-planted seedling traits was intermediate (0.4-0.5) (Table 2), while H2 was higher (0.5-0.8) for seedling traits from normal-planted field trials. H2 for seedling height (in early-planted field trials) was close to zero (0.03), while plant height at maturity was highly heritable (0.9). Based on the averaged data of two replicates within each field trial, low to intermediate correlation (0.1-0.4) was observed with the same seedling trait among locations for early-planted trials.

TABLE 2

Broad-sense heritability ($H^2$) of early- and normal-planted field traits.

| Seedling traits | $H^2$ early planting[a] | $H^2$ normal planting[b] |
|---|---|---|
| Emergence count (EC) | 0.45 | 0.53 |
| Seedling vigor1 (SV1) | 0.52 | 0.57 |
| Seedling vigor2 (SV2) | 0.39 | 0.78 |
| Seedling vigor3 (SV3) | 0.37 | 0.53 |
| Damage rating (DR) | 0.35 | — |
| Seedling height | 0.03 | — |
| Plant height at maturity | 0.93 | — |

[a]Field phenotypes from six early-planted trials.
[b]Field phenotypes from two normal-planted trials.

Composite Interval Mapping of Early-Season Chilling Tolerance

Genetic linkage maps were constructed for each family (NSZ: 1341 markers, 257 RILs; Kao: 1043 markers, 219 RILs; HKZa: 1150 markers, 107 RILs). Map lengths were similar for the NSZ, Kao, and HKZa families (1403 cM, 1381 cM, and 1295 cM, respectively) and individual RILs contained 2-4 crossovers. To map putative chilling tolerance loci, composite interval mapping (CIM) was first conducted in individual families using ~1000-1300 markers and early-planted seedling trait BLUPs (EPEC, EPSV1-3). CIM detected 6-8 QTL, which explained 16-28%, 8-23%, and 12-36% of variation for early-planted seedling traits in the HKZa, Kao, and NSZ families, respectively (Table 3). The QTL on chromosome 4 was detected in all NAM families, with the positive allele inherited from the Chinese founder in each case. CIM of normal-planted seedling BLUPs (NPEC and NPSV1-NPSV3) identified 4-9 QTL contributing to emergence and SV in the HKZa, Kao, and NSZ families, respectively. Few overlaps were observed among QTL detected for early- and normal-planted seedling traits (Tables 3 and 4). As chilling stress varied among locations, QTL mapping was conducted for each field trial separately to check the stability of QTL across locations. The QTL on chromosomes 4 and 7 were detected across families in four and two early-planted trials, respectively.

TABLE 3

Composite interval mapping (CIM) with
early-planted field phenotype BLUPs

| Family[a] | Trait[b] | Peak SNP | QTL Interval (Mb) | LOD[c] | PVE[d] | Additive effect[e] | Known loci[f] | Distance to known loci |
|---|---|---|---|---|---|---|---|---|
| HKZa | EPEC | S6_53866236 | 53-55 | 5.8 | 21.9 | 0.20 | | |
| | EPSV1 | S4_60494734 | 58-62 | 4.3 | 16.9 | −0.14 | Tan1 | 1.8 Mb |
| | EPSV2 | S4_473959 | 0.4-77 | 3.4 | 13.7 | 0.15 | | |
| | | S5_69294666 | 68-69 | 3.9 | 15.3 | 0.13 | | |
| | EPSV3 | S4_597351 | 0.4-13 | 3.1 | 12.7 | 0.09 | | |
| | | S5_69294666 | 68-70 | 3.9 | 15.7 | 0.11 | | |
| | | S7_62611661 | 61-64 | 3.5 | 13.8 | 0.09 | Dw3 | 3 Mb |
| Kao | EPEC | S4_61061060 | 11-63 | 3 | 7.3 | −0.09 | Tan1 | 1.2 Mb |
| | | S8_52136076 | 7-54 | 3 | 6.1 | −0.09 | | |
| | EPSV1 | S2_10876295 | 9-13 | 4.5 | 9.1 | −0.11 | Tan2 | 3 Mb |
| | | S9_52692821 | 51-53 | 4 | 8 | −0.10 | | |
| | EPSV2 | S2_16848234 | 13-55 | 6.8 | 13.4 | −0.12 | | |
| | | S4_61061060 | 11-62 | 4.5 | 9.1 | −0.09 | Tan1 | 1.2 Mb |
| | EPSV3 | S4_62599717 | 61-63 | 3.9 | 7.9 | −0.09 | Tan1 | 0.3 Mb |
| NSZ | EPEC | S2_8451281 | 7-9 | 3.7 | 6.4 | −0.1 | Tan2 | 0.5 Mb |
| | | S3_72404691 | 72-74 | 4.1 | 7.1 | 0.09 | | |
| | | S4_62882446 | 61-64 | 6.2 | 10.5 | −0.13 | Tan1 | 0.6 Mb |
| | EPSV1 | S1_48528744 | 25-53 | 6.4 | 10.9 | −0.14 | | |
| | | S3_72404691 | 11-73 | 3.2 | 5.6 | 0.09 | | |
| | | S4_62882446 | 59-63 | 3.3 | 5.7 | −0.09 | Tan1 | 0.6 Mb |
| | | S7_59412395 | 58-60 | 4.9 | 8.4 | −0.12 | Dw3 | 0.4 Mb |
| | | S9_55625332 | 54-56 | 4.4 | 7.6 | −0.11 | Dw1 | 1.4 Mb |
| | EPSV2 | S1_48528744 | 22-53 | 4.1 | 7.1 | −0.09 | | |
| | | S7_2492149 | 1-3 | 3.2 | 5.5 | −0.08 | | |
| | EPSV3 | S1_48528744 | 21-53 | 4.1 | 7.1 | −0.1 | | |
| | | S7_2492149 | 22-33 | 3.9 | 6.7 | −0.09 | | |

[a]The chilling NAM families: Hong Ke Zi (HKZa), Kaoliang (Kao), and NSZ, Niu Sheng Zui (NSZ).
[b]Early-planted emergence count (EPEC) and seedling vigor (EPSV1-3) were used for CIM.
[c]Logarithm of odds (LOD) score.
[d]Percentage of variation explained (PVE).
[e]Positive or negative effects of the BTx623 allele.
[f]Previously characterized genes colocalizing with the mapped QTL.

35

TABLE 4

Composite interval mapping (CIM) with normal-
planted field phenotype BLUPs.

| Family[a] | Trait[b] | Peak SNP | QTL Interval (Mb) | LOD[c] | PVE[d] | Additive effect[e] | Known loci[f] | Distance to known loci |
|---|---|---|---|---|---|---|---|---|
| HKZa | NPEC | — | — | — | — | — | | |
| | NPSV1 | S1_58632047 | 58-60 | 3.4 | 13.8 | −0.13 | | |
| | | S7_55055485 | 52-57 | 3.7 | 14.6 | −0.16 | Dw3 | 4.8 Mb |
| | NPSV2 | S5_69294666 | 65-70 | 3.3 | 13.3 | 0.13 | | |
| | NPSV3 | S2_4944067 | 4-6 | 3.4 | 13.5 | −0.13 | | |
| | | S5_69720862 | 68-70 | 4.2 | 16.5 | 0.13 | | |
| Kao | NPEC | S7_57372955 | 56-58 | 4.1 | 8.2 | −0.10 | Dw3 | 2.4 Mb |
| | | S10_3575834 | 18-54 | 3.1 | 6.4 | 0.10 | | |
| | NPSV1 | S1_68309753 | 64-71 | 3.3 | 6.7 | −0.10 | | |
| | | S2_63030650 | 62-65 | 3.6 | 7.3 | −0.16 | | |
| | | S3_13167621 | 12-14 | 11.3 | 21.2 | 0.28 | | |
| | | S7_56368290 | 55-57 | 5.4 | 10.8 | −0.18 | Dw3 | 3.4 Mb |
| | NPSV2 | S1_2859329 | 2-6 | 3.7 | 7.5 | −0.15 | | |
| | | S2_16406623 | 13-18 | 6.1 | 12 | −0.18 | | |
| | | S3_13097936 | 12-14 | 9.8 | 18.6 | 0.24 | | |
| | | S10_3240955 | 17-53 | 3.5 | 7 | 0.15 | | |
| | NPSV3 | S2_16406623 | 15-55 | 3.7 | 7.6 | −0.12 | | |
| | | S3_13167621 | 12-14 | 13.2 | 24.2 | 0.22 | | |
| | | S7_57460966 | 13-62 | 3.3 | 6.7 | −0.1 | Dw3 | 2.3 Mb |
| | | S10_3536844 | 0.3-60 | 3.3 | 6.7 | 0.12 | | |
| NSZ | NPEC | S7_39531433 | 12-56 | 2.9 | 5 | −0.07 | | |
| | NPSV1 | S1_58632047 | 56-59 | 7 | 11.9 | −0.16 | | |
| | | S7_58340519 | 57-59 | 5.4 | 9.1 | −0.15 | Dw3 | 1.5 Mb |
| | | S9_56657651 | 56-58 | 3 | 5.3 | −0.11 | Dw1 | 0.4 Mb |

TABLE 4-continued

| | | | Composite interval mapping (CIM) with normal-planted field phenotype BLUPs. | | | | | |
|---|---|---|---|---|---|---|---|---|
| Family[a] | Trait[b] | Peak SNP | QTL Interval (Mb) | LOD[c] | PVE[d] | Additive effect[e] | Known loci[f] | Distance to known loci |
| NPSV2 | S1_26240607 | 21-52 | 7.5 | 12.5 | −0.17 | | |
| | S2_66319995 | 58-70 | 3 | 5.2 | −0.1 | | |
| | S3_73329070 | 1-73 | 4 | 6.9 | 0.12 | | |
| | S7_27327629 | 14-53 | 3.5 | 6 | −0.12 | | |
| NPSV3 | S1_26240607 | 21-54 | 3.3 | 5.7 | −0.1 | | |
| | S3_73329070 | 0.5-73 | 3 | 5.3 | 0.10 | | |
| | S9_50757859 | 0.5-50 | 2.9 | 5.1 | −0.1 | | |

[a]The chilling NAM families: Hong Ke Zi (HKZa), Kaoliang (Kao), and NSZ, Niu Sheng Zui (NSZ).
[b]Normal-planted emergence count (NPEC) and seedling vigor (NPSV1-3) were used for CIM.
[c]Logarithm of odds (LOD) score.
[d]Percentage of variation explained (PVE).
[e]Positive or negative effects of the BTx623 allele.
[f]Previously characterized genes colocalizing with the mapped QTL.

Joint Linkage Mapping of Early-Season Chilling Tolerance

To leverage data across families, JLM was performed with 43,320 SNPs and field phenotypes from 750 RILs (including the HKZb family) (FIG. 3A-E). JLM of seedling trait BLUPs (derived from ~12,000 early-planted plots) identified 15 QTL, seven of which were detected for multiple seedling traits (FIG. 3D and Table 5). Each QTL explained 1-9% of phenotypic variation. In total, the QTL explained 21-41% variation for emergence and seedling vigor. Positive alleles were inherited from the Chinese founders, except for the allele at chromosome 3. The QTL on chromosomes 2 and 4 were detected for every early-planted seedling trait. The chromosome 1 and 5 QTL were detected with all seedling vigor traits, while chromosome 7 and 9 were mapped with two early-planted seedling traits (FIG. 3D). The QTL on chromosomes 2 and 4 colocalized (<1 Mb) with classical tannin genes, Tan2 and Tan1, and chromosomes 7 and 9 loci colocalized with classical dwarfing genes, Dw3 and Dw1. JLM of normal-planted traits mapped different QTL for emergence, but few overlapped with QTL for early-planted seedling vigor (FIGS. 3C and Table 6).

To check the stability of QTL across locations and years, JLM was performed separately by location. The QTL on chromosome 9 was detected in three early-planted locations, while QTL on chromosomes 2 and 7 were mapped in two locations (FIG. 3B). The chromosome 4 QTL was consistently detected across early-planted field locations and years. The only exception was the MN17 field trial, which emerged under optimal conditions and experienced chilling one week later, where the chromosome 4 QTL was not detected (FIG. 3B). Among the loci detected with JLM of field phenotypes from early- and normal-planted individual field trials (FIGS. 3A-B), few overlaps were observed.

The most significant and consistent QTL (qSbCT04.62; Table 5) colocalized with CBF gene Sobic.004G283201 (120 kb from the peak SNP), ortholog of the canonical Arabidopsis cold acclimation regulator CBF1. However, sequencing of the CBF gene from the Chinese founders revealed no change in their predicted peptide relative to the BTx623 reference sequence.

TABLE 5

| | | | | | | Distance to | |
|---|---|---|---|---|---|---|---|
| | | | | | Known | known | QTL |
| Trait[a] | QTL | QTL_SNP | PVE[b] | Additive effect[c] | loci[d] | loci | name[e] |
| EPEC | qSbEPEC_4-62 | S4_62368531 | 9.2 | −0.08 | Tan1 | 53 kb | qSbCT04.62 |
| | qSbEPEC_3-72 | S3_72791601 | 2.4 | 0.01 | | | |
| | qSbEPEC_2-08 | S2_8672301 | 2.8 | −0.06 | Tan2 | 0.6 Mb | qSbCT02.08 |
| | qSbEPEC_7-59 | S7_59915577 | 3.3 | −0.08 | Dw3 | 93 kb | qSbCT07.59 |
| | qSbEPEC_9-58 | S9_58070153 | 1.5 | −0.04 | Dw1 | 1 Mb | qSbCT09.57 |
| | qSbEPEC_3-01 | S3_1779472 | 1.4 | 0.03 | | | |
| EPSV1 | qSbEPSV1_4-62 | S4_62368531 | 5.4 | −0.07 | Tan1 | 53 kb | qSbCT04.62 |
| | qSbEPSV1_9-55 | S9_55625332 | 5 | −0.07 | Dw1 | 1.4 Mb | qSbCT09.57 |
| | qSbEPSV1_1-57 | S1_57941435 | 5.7 | −0.11 | | | qSbCT01.57 |
| | qSbEPSV1_1-05 | S1_5730743 | 3.9 | −0.06 | | | qSbCT01.06 |
| | qSbEPSV1_7-12 | S7_12580350 | 4.5 | −0.06 | | | qSbCT07.10 |
| | qSbEPSV1_2-09 | S2_9260382 | 3.9 | −0.06 | Tan2 | 1.2 Mb | qSbCT02.08 |
| | qSbEPSV1_3-01 | S3_1447612 | 1.4 | 0.03 | | | |
| | qSbEPSV1_5-04 | S5_4403613 | 1.6 | −0.04 | | | qSbCT05.04 |
| | qSbEPSV1_1-13 | S1_13526795 | 3.5 | −0.1 | | | qSbCT01.13 |
| | qSbEPSV1_7-59 | S7_59290017 | 5.6 | −0.08 | Dw3 | 0.5 Mb | qSbCT07.59 |
| EPSV2 | qSbEPSV2_4-62 | S4_62455479 | 5.8 | −0.05 | Tan1 | 0.1 Mb | qSbCT04.62 |
| | qSbEPSV2_2-09 | S2_9218398 | 6 | −0.05 | Tan2 | 1.2 Mb | qSbCT02.08 |
| | qSbEPSV2_5-04 | S5_4284787 | 3.6 | −0.04 | | | qSbCT05.04 |
| | qSbEPSV2_1-13 | S1_13188261 | 4.6 | −0.06 | | | qSbCT01.13 |

Joint linkage mapping (JLM) with early-planted field phenotypes.

TABLE 5-continued

Joint linkage mapping (JLM) with early-planted field phenotypes.

| Trait[a] | QTL | QTL_SNP | PVE[b] | Additive effect[c] | Known loci[d] | Distance to known loci | QTL name[e] |
|---|---|---|---|---|---|---|---|
| | qSbEPSV2_1-06 | S1_6902771 | 4.8 | −0.05 | | | qSbCT01.06 |
| | qSbEPSV2_7-08 | S7_8916696 | 2.1 | −0.05 | | | qSbCT07.10 |
| EPSV3 | qSbEPSV3_2-09 | S2_9218398 | 6.8 | −0.05 | Tan2 | 1.2 Mb | qSbCT02.08 |
| | qSbEPSV3_4-62 | S4_62455479 | 5.2 | −0.05 | Tan1 | 0.1 Mb | qSbCT04.62 |
| | qSbEPSV3_1-09 | S1_9756192 | 5.2 | −0.06 | | | qSbCT01.13 |
| | qSbEPSV3_1-26 | S1_26930469 | 4.3 | −0.05 | | | |
| | qSbEPSV3_5-04 | S5_4284787 | 3.5 | −0.03 | | | qSbCT05.04 |

[a]Early-planted emergence count (EPEC) and seedling vigor (EPSV1-3) BLUPS were used for JLM.
[b]Percentage of variation explained (PVE).
[c]Positive or negative effects of the BTx623 allele.
[d]Previously characterized genes colocalizing with the mapped QTL.
[e]QTL in 2 Mb interval, detected with different seedling traits, were assigned a common name.

TABLE 6

Joint linkage mapping (JLM) with normal-planted field phenotype BLUPs.

| Trait[a] | QTL | QTL_SNP | PVE[b] | Additive effect[c] | Known loci[d] | Distance to known loci | QTL name[e] |
|---|---|---|---|---|---|---|---|
| NPEC | qSbNPEC_7-39 | S7_39135105 | 4.3 | −0.05 | | | |
| | qSbNPEC_5-65 | S5_65643264 | 3.5 | 0.09 | | | |
| NPSV1 | qSbNPSV1_3-13 | S3_13282550 | 6.8 | 0.09 | | | |
| | qSbNPSV1_1-57 | S1_57941435 | 4.2 | −0.14 | | | qSbCT01.57 |
| | qSbNPSV1_7-57 | S7_57053050 | 5.1 | −0.09 | Dw3 | 2.8 Mb | qSbCT07.59 |
| | qSbNPSV1_9-53 | S9_53265143 | 1 | −0.04 | Dw1 | 3.8 Mb | qSbCT09.57 |
| | qSbNPSV1_2-62 | S2_62962601 | 4.2 | −0.07 | | | |
| | qSbNPSV1_1-05 | S1_5754842 | 4.3 | −0.07 | | | qSbCT01.06 |
| | qSbNPSV1_10-03 | S10_3699364 | 2.7 | 0.14 | | | |
| | qSbNPSV1_1-11 | S1_11764852 | 4.8 | −0.10 | | | qSbCT01.13 |
| NPSV2 | qSbNPSV2_1-07 | S1_7625404 | 6 | −0.08 | | | qSbCT01.06 |
| | qSbNPSV2_7-30 | S7_30184611 | 4.5 | −0.07 | | | |
| | qSbNPSV2_1-57 | S1_57941435 | 4.1 | −0.13 | | | |
| | qSbNPSV2_10-03 | S10_3686338 | 3.1 | 0.16 | | | |
| | qSbNPSV2_2-64 | S2_64314153 | 3.2 | −0.06 | | | |
| | qSbNPSV2_2-25 | S2_25130132 | 3.8 | −0.06 | | | |
| | qSbNPSV2_3-13 | S3_13759646 | 3.7 | 0.09 | | | |
| | qSbNPSV2_1-14 | S1_14774558 | 3 | −0.08 | | | qSbCT01.13 |
| | qSbNPSV2_9-53 | S9_53265132 | 0.5 | −0.03 | Dw1 | 3.7 Mb | qSbCT09.57 |
| | qSbNPSV2_3-13 | S3_13245510 | 5 | 0.07 | | | |
| NPSV3 | qSbNPSV4_3-13 | S3_13282550 | 6.2 | 0.07 | | | |
| | qSbNPSV4_2-64 | S2_64314153 | 3.7 | −0.05 | | | |
| | qSbNPSV4_10-04 | S10_4652526 | 2.6 | 0.14 | | | |
| | qSbNPSV4_7-41 | S7_41996273 | 4.4 | −0.06 | | | |
| | qSbNPSV4_7-60 | S7_60102977 | 3.6 | −0.08 | Dw3 | 0.2 Mb | |
| | qSbNPSV4_1-07 | S1_7784945 | 3.9 | −0.06 | | | qSbCT01.06 |
| | qSbNPSV4_1-11 | S1_11801181 | 4.8 | −0.08 | | | qSbCT01.13 |
| | qSbNPSV4_4-57 | S4_57456389 | 2 | 0.1 | Tan1 | 4 Mb | |
| | qSbNPSV4_1-57 | S1_57941435 | 2.1 | −0.1 | | | |

[a]Normal-planted emergence count (EPEC) and seedling vigor (EPSV1-3) BLUPS were used for JLM.
[b]Percentage of variation explained (PVE).
[c]Positive or negative effects of the BTx623 allele.
[d]Previously characterized genes colocalizing with the mapped QTL.
[e]QTL in 2 Mb interval, detected with different seedling traits, were assigned a common name.

Mapping for Agronomic Traits and Grain Tannin

CIM and JLM was conducted to identify loci underlying plant height, flowering time, and grain tannins. CIM detected three plant height QTL in the HKZa family (Table 7), and two each in the NSZ and Kao families, explaining 30-82% of plant height variation. Two plant height QTL, detected on chromosomes 7 and 9, colocalized with classical dwarfing genes Dw3 and Dw1, respectively. JLM identified six plant height QTL, of which alleles at four and two QTL contained negative and positive effects, respectively (FIGS. 3C and Table 8). Three QTL of major effect explained 85% plant height variation. Major height loci were 12 kb and 0.1 Mb from Dw3 and Dw1 genes, respectively.

Figure 3:
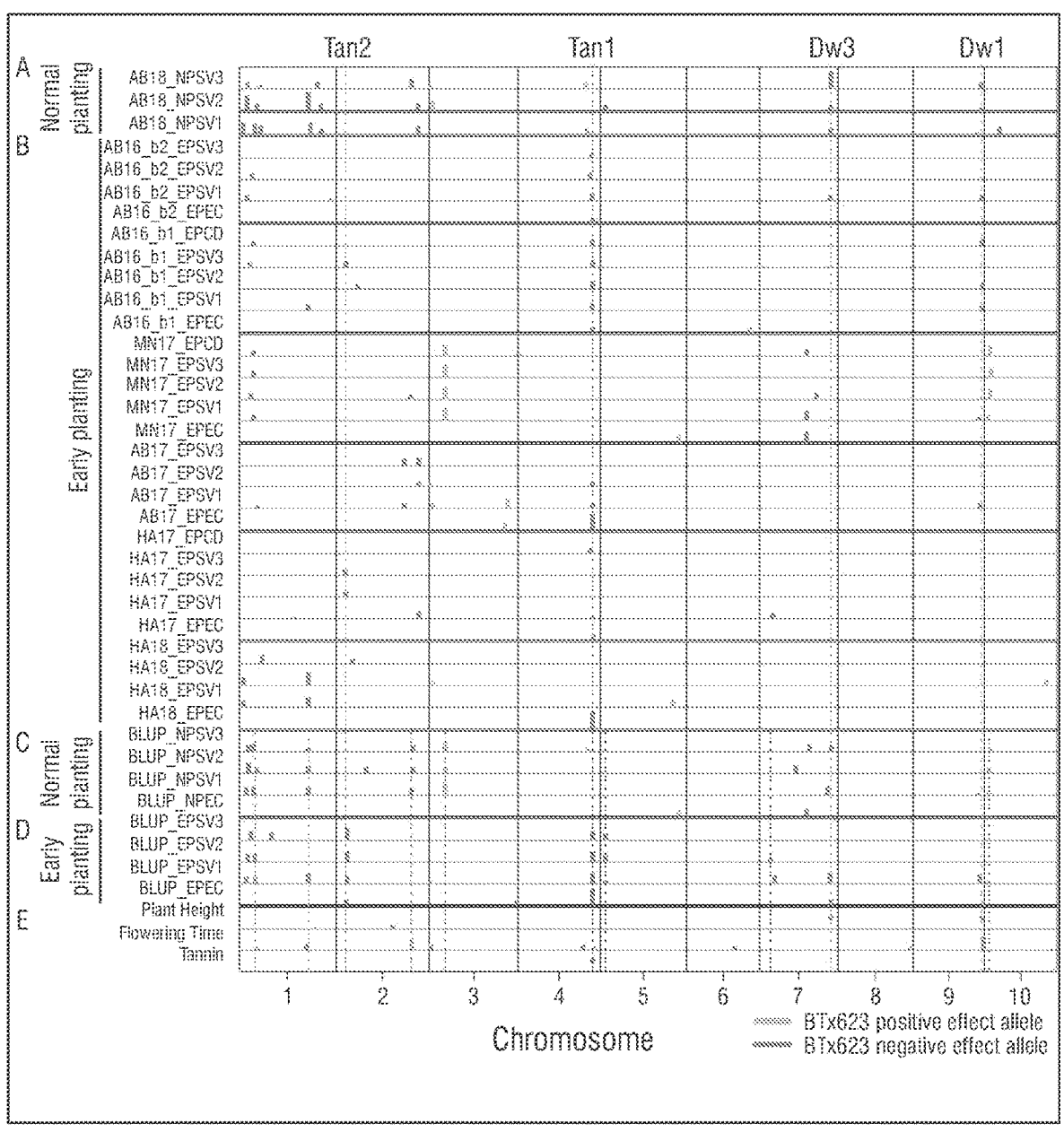
FIG. 3 shows joint linkage mapping (JLM) of chilling tolerance and undesirable traits. JLM of seedling traits from individual (A) normal (NP) and (B) early planting (EP) field trials. Field location and year were included as prefixes for each seedling trait. Five NP traits that failed to detect QTL were excluded from the figure but used for calculating NP seedling trait BLUPs. JLM with seedling trait BLUPs, generated with ~75,000 data points from ~16,000 field plots, from (C) normal and (D) early planting. Additionally, (E) JLM of plant height, flowering time, and grain tannins were included. Classical dwarfing and tannin genes were noted with gray dashed lines. Chilling tolerance QTL detected under early planting are noted with blue dashed lines and green lines noted chilling tolerance QTL detected under both early and normal planting. The QTL under normal planting were noted with red dashed lines. Positive or negative effects of the BTx623 allele was indicated in orange or blue colors, respectively. The percentage of variation explained is proportional to the width of the box for each locus and loci explaining phenotypic variation >10% are noted with circles. Abbreviations: EC, emergence count; SV1-3, seedling vigor1-3; CD, chilling damage.

Although flowering time varied little among the founders (FIG. 1E), transgressive segregation enabled detection of seven flowering time loci (four, two, and one QTL in the NSZ, Kao, and HKZa families, respectively) which explain 20-28% of variation (Table 7). JLM with flowering time detected 10 QTL that explained 33% variation (FIGS. 3C and Table 8), three of which co-localized with previously identified flowering time/maturity genes, TOC1/CN2, ma1, and CN8. CIM of grain tannin presence/absence identified a major QTL on chromosome 4 in each family, with the Chinese parent conferring tannin presence allele in each case. The locus colocalizing with Tan1 explained 77, 34, and 100% of grain tannin variation in the HKZa, NSZ, and Kao families, respectively (Table 7). JLM identified two tannin loci, one mapped ~70 kb from Tan1 and the other mapped ~1.4 Mb from an earlier reported Tan2 candidate gene (Table 8).

validated by the precise mapping (<100 kb) of cloned dwarfing (Dw1 and Dw3) and tannin (Tan1) genes (FIG. 3, Table 8). Similarly, several major QTL (qSbCT04.62, qSbCT02.08, qSbCT07.59, and qSbCT09.57) were encompassed within the QTL intervals detected previously (Table 9). Notably, however, the greater population size (~4-5-fold) and marker density (>100-fold) with NAM relative to earlier studies greatly improved the mapping resolution (>10-fold;

TABLE 7

Composite interval mapping (CIM) of agronomic traits and grain tannins.

| Family[a] | Trait[b] | Peak SNP | QTL Interval (Mb) | LOD[c] | PVE[d] | Additive effect[e] | Known loci[f] | Distance to known loci |
|---|---|---|---|---|---|---|---|---|
| HKZa | PHT | S1_68318606 | 67-71 | 4.5 | 18 | 17 | | |
| | | S7_60216181 | 60-61 | 12 | 41 | −30 | Dw3 | 0.3 Mb |
| | | S9_57804067 | 56-58 | 6 | 23 | −18 | Dw1 | 0.7 Mb |
| | FT | S3_13889853 | 1-15 | 4 | 16 | 5 | | |
| | | S10_56467046 | 56-57 | 3 | 12 | −3 | | |
| | Tannins | S4_61061060 | 60-62 | 34 | 77 | −0.8 | Tan1 | 1.2 Mb |
| NSZ | PHT | S7_59953003 | 59-60 | 35 | 46 | −38 | Dw3 | 0.1 Mb |
| | | S9_56657651 | 56-57 | 22 | 32 | −29 | Dw1 | 0.4 Mb |
| | FT | S1_59369684 | 58-61 | 4 | 6 | −3 | | |
| | | S2_63186100 | 60-65 | 5 | 8 | 4 | | |
| | | S8_61537016 | 59-62 | 3 | 6 | 2 | | |
| | | S9_58670296 | 58-59 | 4 | 7 | −3 | | |
| | Tannins | S4_61212673 | 60-62 | 23 | 34 | −0.8 | Tan1 | 1.1 Mb |
| Kao | PHT | S7_56844702 | 56-64 | 6 | 11 | −28 | Dw3 | 3 Mb |
| | | S9_51987531 | 51-53 | 10 | 19 | −36 | | |
| | FT | S2_66179497 | 65-67 | 5 | 10 | 3 | | |
| | | S10_54171866 | 53-55 | 5 | 10 | −3 | | |
| | Tannins | S4_62599717 | 61-63 | 1450 | 100 | −0.92 | Tan1 | 0.8 Mb |

[a]The NAM population families referred by the alternate NAM founder.
[b]Plant height (PHT), flowering time (FT), and grain tannin phenotypes were used for CIM.
[c]Logarithm of odds (LOD).
[d]Percentage of variation explained (PVE).
[e]Positive or negative effects of the BTx623 allele.
[f]Previously characterized genes colocalizing with the mapped QTL.

TABLE 8

Joint linkage mapping of plant height, flowering time, and grain tannins.

| Trait[a] | QTL | QTL_SNP | PVE[b] | Additive effect[c] | Known loci[d] | Distance to known loci |
|---|---|---|---|---|---|---|
| PHT | qSbPHT_7-59 | S7_59675001 | 32 | −21 | Dw3 | 0.1 Mb |
| | qSbPHT_9-57 | S9_57051085 | 20 | −17 | Dw1 | 12 kb |
| | qSbPHT_1-67 | S1_67896587 | 0.5 | 0.7 | | |
| | qSbPHT_2-47 | S2_47294140 | 2 | −5 | | |
| | qSbPHT_7-59 | S7_59956049 | 33 | −21 | Dw3 | 0.1 Mb |
| | qSbPHT_1-63 | S1_63253487 | 1 | 7 | | |
| FT | qSbFT_9-58 | S9_58468998 | 8 | −1.5 | CN8 | 3.5 Mb |
| | qSbFT_2-64 | S2_63261883 | 6 | 1.4 | | |
| | qSbFT_8-59 | S8_59740114 | 2 | 0.9 | | |
| | qSbFT_1-56 | S1_56436041 | 3 | −1 | | |
| | qSbFT_3-01 | S3_1441099 | 3.03 | −0.96 | | |
| | qSbFT_4-63 | S4_63556402 | 2.01 | 0.82 | | |
| | qSbFT_4-54 | S4_54231126 | 3.11 | −1.32 | CN2 | 8.6 Mb |
| | qSbFT_1-14 | S1_14862315 | 1.97 | 0.92 | | |
| | qSbFT_10-56 | S10_56045853 | 0.69 | −0.4 | | |
| | qSbFT_6-40 | S6_40299229 | 2.55 | −0.89 | Ma1 | 5 kb |
| Tannin | qSbTan_4-62 | S4_62389178 | 72 | −0.4 | Tan1 | 73 kb |
| | qSbTan_4-62 | S4_62261292 | 46 | −0.4 | Tan1 | 54 kb |
| | qSbTan_4-61 | S4_61963287 | 22 | −0.3 | Tan1 | 0.3 Mb |
| | qSbTan_2-09 | S2_9390193 | 0.06 | 0.02 | Tan2 | 1.4 Mb |
| | qSbTan_10-59 | S10_59593345 | 2 | 0.2 | | |

[a]Plant height (PHT), flowering time (FT), and grain tannin phenotypes were used for JLM.
[b]Percentage of variation explained (PVE).
[c]Positive or negative effects of the BTx623 allele.
[d]Previously characterized PHT, FT, and grain tannin genes colocalizing with the mapped QTL.

The quality of the chilling NAM resource (i.e. RILs and corresponding SNP genotypes) developed in our study is Table 9) and power (i.e. several additional loci identified). Family structure and LD decay of the chilling NAM population generally matches expectations based on population design and observations from previous NAM populations. Genotypic (FIG. 2A) and phenotypic similarity of HKZa and HKZb RILs suggest that the differentiation is due to residual heterozygosity in the HKZ founder or pollen contamination from another Chinese accession. Given that inbreeding coefficient (F) is similar between Chinese parents (HKZ 0.8; Kao 0.9; NSZ 0.76; and BTx623 0.92) and parent-unique SNPs are absent only in the HKZb family, the HKZb RILs were most likely derived from pollen contamination. However, uncertainty regarding the pedigree of HKZb RILs does not diminish their usefulness as a part of the NAM resource (e.g. FIG. 3).

QTL mapping from multi-environment trials clearly identified a major oligogenic component of chilling tolerance (FIG. 3), consistent with previous work. In keeping with the breeding goals, we considered all QTL that controlled performance under chilling stress (emergence, seedling vigor, or both) as chilling tolerance loci (Table 5), regardless of whether they also controlled performance under normal conditions. As chilling tolerance trials were conducted in a field environment, heritability and QTL effect sizes (Tables 2 and 5) were somewhat reduced compared to previous experiments under controlled conditions. While replicability of field phenotyping for abiotic stress is a major challenge, observing plant performance under field conditions may increase the likelihood that genetic discoveries will translate to farmer fields. A common limitation for molecular breeding of stress tolerance has been a lack of QTL stability (i.e. QTL×environment interaction). The overlapping of multi-environment chilling tolerance QTL from this study with QTL previously identified in the fields in Texas and Indiana (Table 9) provides evidence of their stability across a wide range of early-season chilling scenarios.

The Genetic Basis of Early-Season Chilling Tolerance

Molecular networks for cold sensing and response appear to be largely conserved across plants. These findings are consistent with long-standing observations of homologous variation in cold tolerance across diverse grasses, including sorghum. For this reason, we considered whether NAM provides evidence that chilling tolerance in Chinese sorghum is due to derived variation at canonical cold tolerance genes (e.g. CBFs, COLD1, SENSITIVE TO FREEZING2, etc). Overall, we found little evidence that the chilling tolerance in Chinese sorghum is due to variation in canonical cold regulators (i.e. little localization between QTL and sorghum orthologs of known plant cold tolerance genes). For instance, the (ʹBF gene near the chilling tolerance QTL on chromosome 4 shows no coding sequence differences among the founder lines and a previous study showed no chilling-responsive expression of this (BF in chilling-tolerant NSZ. These findings suggest that a different closely linked gene, or the nearby Tan1 gene, underlie this chilling tolerance QTL. No other QTL colocalized with orthologs of known plant cold tolerance genes.

The chilling tolerance QTL observed in our study may represent novel chilling tolerance mechanisms in sorghum, or conserved mechanisms not yet described in model plants. Fine-mapping and positional cloning of each chilling tolerance QTL will be needed to address these or other hypotheses on the molecular basis of chilling tolerance in sorghum. Still, the genetic architecture provides some potential clues. Surprisingly, chilling tolerance QTL colocalized closely with classical tannin (Tan1 and Tan2) and dwarfing genes (Dw1 and Dw3) (FIG. 3), four of the five most important genes under selection by US sorghum breeders in the 20th century (the fifth important gene, not colocalizing with chilling tolerance QTL is Maturity1). This finding contradicted our original hypothesis of weak coupling-phase linkage of chilling susceptibility alleles with nontannin and

TABLE 9

Comparison of chilling tolerance QTL with previous mapping studies.

| Chr[a] | Position[b] | Trait[c] | Tagging marker | Interval (Mb)[d] | Reference[e] | NAM QTL[f] |
|---|---|---|---|---|---|---|
| 1 | 66.04 | SV | Xtxp58 | 19-59 | Knoll et al. 2007 | qSbCT01.57 |
| 1 | 57.36 | Emer, SV | Xtxp43 | 57-59 | Knoll et al. 2007 | qSbCT01.57 |
| 2 | 4.98 | Emer, SV | Xtxp211 | 4-27 | Knoll et al. 2007 | qSbCT02.08 |
| 4 | 61.86 | Emer, SV | Xtxp51 | 61-68 | Knoll et al. 2007 | qSbCT04.62 |
| 5 | 51.77 | ESV | Xtxp14 | — | Knoll et al. 2007 | — |
| 9 | 4.2 | Emer, SV | Xtxp287 | — | Knoll et al. 2007 | — |
| 1 | 4.05 | FEarlyGerm1.1 | Xsbarslbk1.04 | 0-7 | Burow et al. 2010 | qSbCT01.06 |
| 1 | 68.33 | FEarlyGerm1.2 | Xtxp279 | 65-71 | Burow et al. 2010 | — |
| 2 | 56.01 | Germ12C-2.1 | Xsbarslbk_2.56 | 44-60 | Burow et al. 2010 | — |
| 4 | 61.86 | FEarlyGerm4.1 | Xtxp212 | 59-65 | Burow et al. 2010 | qSbCT04.62 |
| 4 | | FearlyVigor4.1 | Xtxp327 | — | Burow et al. 2010 | |
| 7 | | FEarlyGerm7.1 | Xtxp218 | 7-57 | Burow et al. 2010 | qSbCT07.59 |
| 7 | | FEarlyGerm7.1 | Xtxp159 | 7-57 | Burow et al. 2010 | qSbCT07.59 |
| 9 | 7.07 | FEarlyGerm9.1 | Xsbarslbk9.07 | 2-44 | Burow et al. 2010 | — |
| 9 | 47.75 | FEarlyGerm9.2 | Xtxp010 | 44-57 | Burow et al. 2010 | qSbCT09.57 |
| 9 | 52.85 | FEarlyGerm9.3 | Xsbarslbk_9.53 | 52-57 | Burow et al. 2010 | qSbCT09.57 |
| 7 | 56.99 | Emer (GWAS) | S7_56998511 | | Upadhyaya et al. 2015 | qSbCT07.59 |
| 4 | 49.4 | Emer | sPb-4851 | 13-40 | Fiedler et al. 2012 | — |
| 1 | 57.36 | Emer | Xtxp43 | 55-57 | Fiedler et al. 2012 | qSbCT01.57 |

[a]Chromosomes with previously reported chilling tolerance QTL.
[b]Genetic distance of the previously mapped QTL on the BTx623 reference genome SbV3.1.
[c]Seedling traits mapping the previous QTL.
[d]QTL interval derived using flanking markers of previously mapped QTL.
[e]Previous biparental mapping studies to map early-season chilling tolerance.
[f]Overlapping chilling tolerance QTL between the chilling NAM and previous biparental populations.

dwarfing alleles. The colocalization itself could be due to (i) tight linkage (e.g. <1 Mb) of chilling tolerance loci to classical tannin and dwarfing loci or (ii) pleiotropic effects of classical tannin and dwarfing loci on chilling tolerance.

First we considered whether coinheritance of tannin and chilling tolerance alleles could be due to a pleiotropic effect of seed pigmentation regulators (Tan1 and Tan2) on chilling tolerance. Although BTx623 and Chinese parents all harbor functional Tan2 alleles (based on complementary dominance of tannin genes), the chilling tolerance QTL near Tan2 could be due to allelic variation at Tan2 that does not alter grain tannins. A conserved MBW ternary complex controls biosynthesis of flavonoids and tannins in plants via interactions of Myb and bHLH transcription factors with a WD40 transcriptional regulator. Among sorghum tannin genes, Tan1 encodes the WD40 component and Tan2 colocalizes with the bHLH transcription factor (Sobic.002G076600) orthologous to *Arabidopsis* TRANSPARENT TESTA8 (AtTT8) and rice red grain gene (OsRc). The MBW complex has pleiotropic effects on abscisic acid-mediated seed dormancy and polyphenol-mediated protection from soil-borne pathogens, which could contribute to emergence and seedling vigor under chilling. The chilling tolerance QTL qSbCT02.08 detected in JLM of nontannin RILs suggests that early-season chilling tolerance does not require seed tannins, even if the trait is under the control of the MBW complex. The existence of a Chinese accession Gai Gaoliang (PI 610727) that is chilling-tolerant but lacks grain tannins supports this hypothesis.

Next we considered whether plant height alleles (Dw1 and Dw3) could have pleiotropic effects on chilling tolerance that explain their colocalization with qSbCT07.59 and qSbCT09.57. Dw1, which colocalized with qSbCT09.57, encodes a novel component of brassinosteroid (BR) signaling. BR signaling controls cold tolerance mechanisms in tomato and *Arabidopsis* so colocalization of qSbCT09.57 with Dw1 could reflect a pleiotropic chilling tolerance effect of DW1 BR signaling. Dw3, which colocalized with qSbCT07.59, encodes an auxin transporter. However, to our knowledge, no reports have demonstrated a role of auxin signaling in chilling tolerance.

Origins and Consequences of the Genetic Architecture of Chilling Tolerance

Figure 4A:
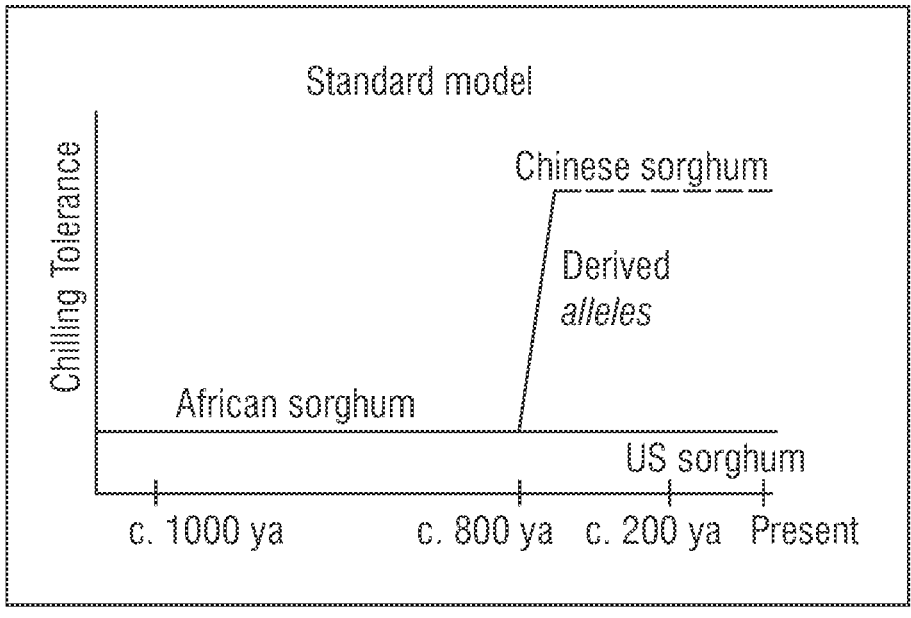
FIG. 4 shows evolutionary origin and agronomic effects of chilling tolerance. (A) Standard model: African sorghums are chilling sensitive based on their tropical origin, sorghum dispersed into northern China (c. 800 years ago) has adapted to chilling while the US sorghums derived from African sorghums remain chilling-sensitive. (B) Based on the genetic architecture of early-season chilling tolerance, we revised the model to explain chilling sensitivity of US sorghums. Coinheritance of chilling tolerance loci with wildtype alleles of classical dwarfing (Dw1 and Dw3) and tannin (Tan1 and Tan2) genes suggest tropical-origin sorghums are chilling-tolerant. Inadvertent selection of chilling-sensitive alleles with favorable dwarfing (dw1 and dw3) and nontannin (tan1 and tan2) alleles resulted in persistence of chilling sensitivity in US sorghums, despite breeding for chilling tolerance over the past 50 years.

Chilling sensitivity of US sorghum has generally been understood to be a result of sorghum's tropical origin (FIG. 4A), in keeping with a classic phytogeographic model. Under this model, ancestrally chilling-sensitive African sorghums would have adapted to cold upon diffusion to temperate regions in central Asia and northern China (c. 800 years ago) due to derived alleles. However, our finding that chilling tolerance alleles coinherited with the ancestral wildtype alleles of classical tannin and dwarfing genes, which are widespread in both African and Chinese sorghums, suggests this model may be incorrect.

Figure 4B:
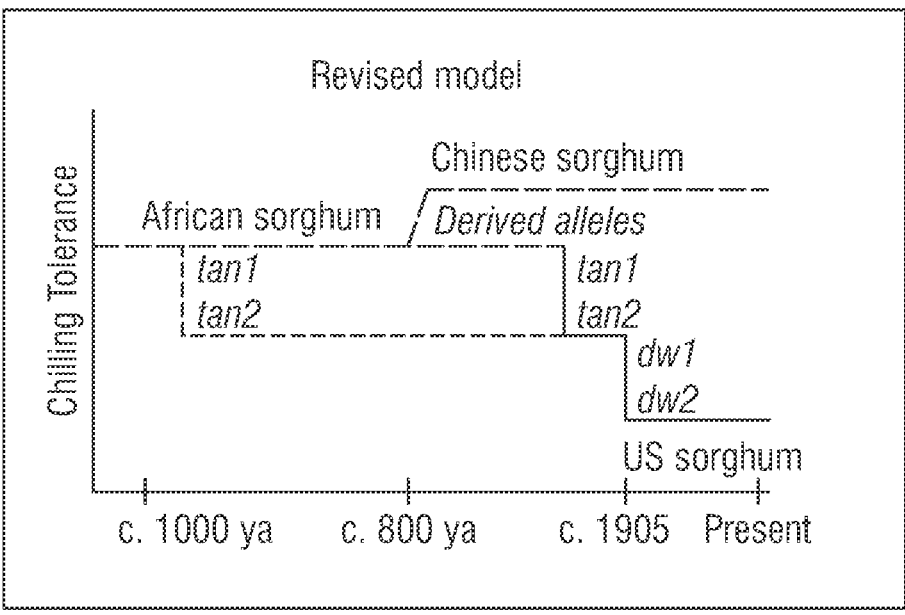
Figure 5A:
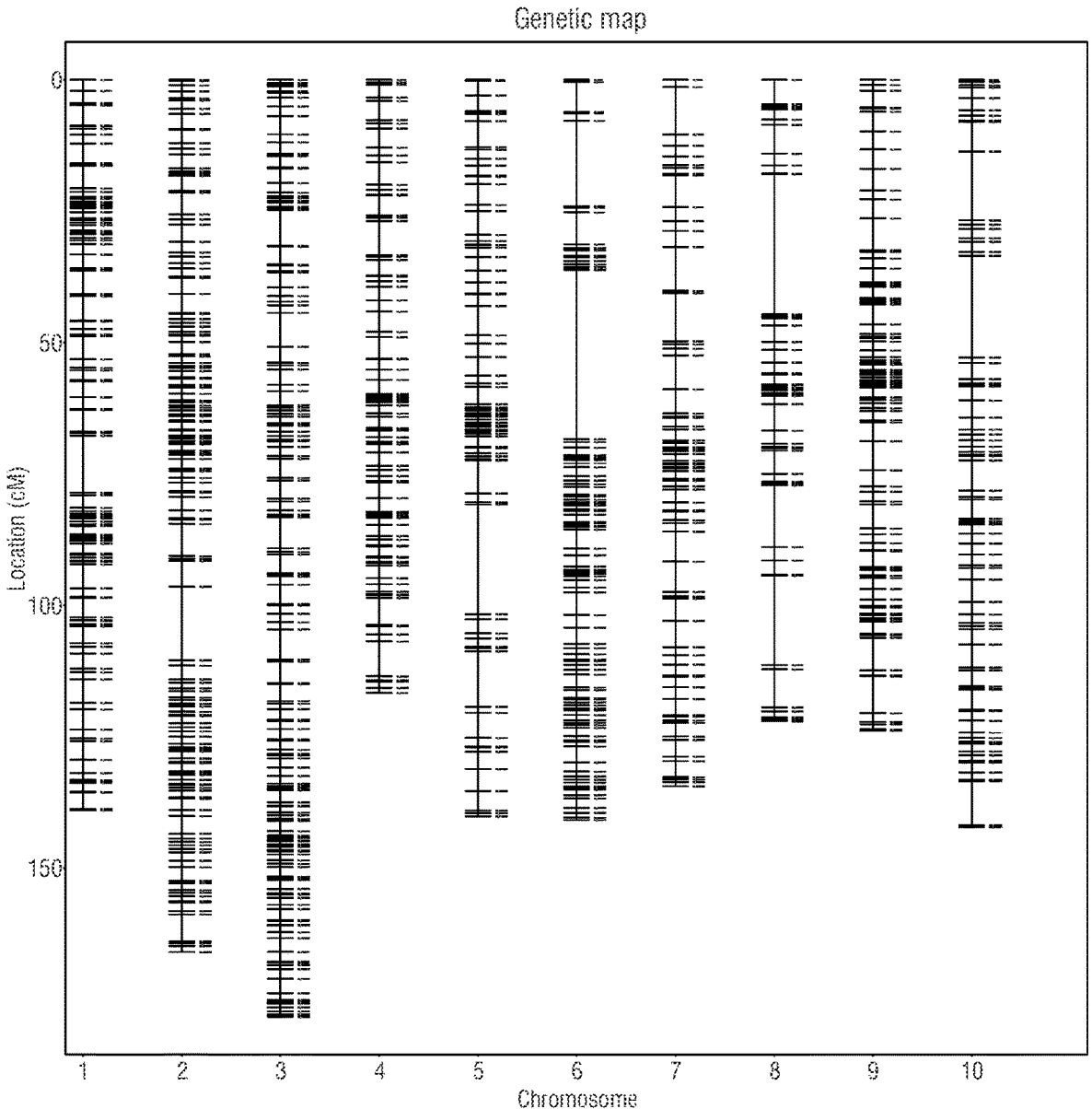
FIG. 5 shows the genetic linkage maps of the NAM families. Genetic linkage maps were generated individually for each NAM family, (A) NSZ: 1341 markers and 257 RILs, (B) HKZ: 1150 markers and 107 RILs, and (C) Kao: 1043 markers and 219 RILs using R/qtl.
Figure 5B:
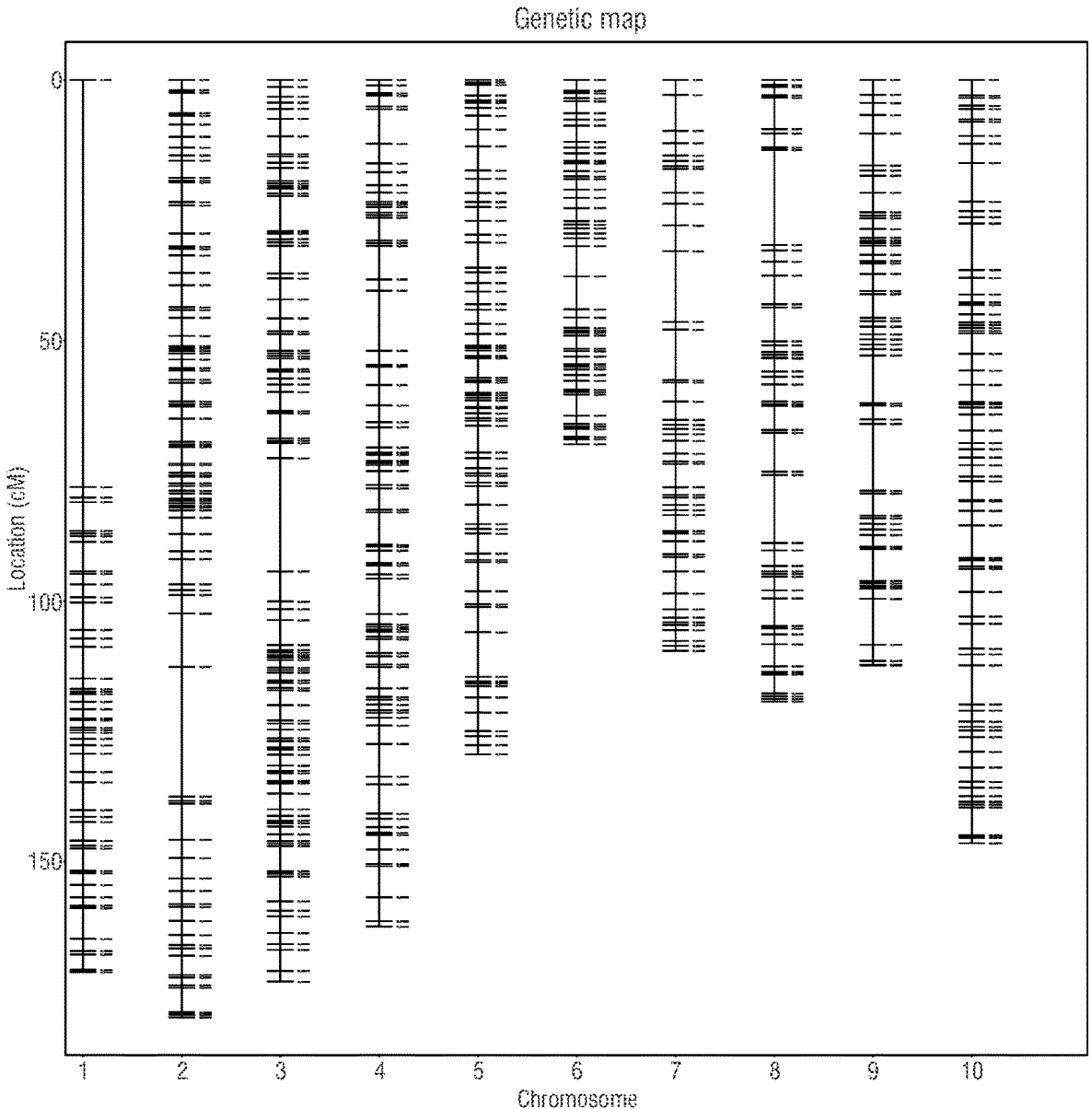
Figure 5C:
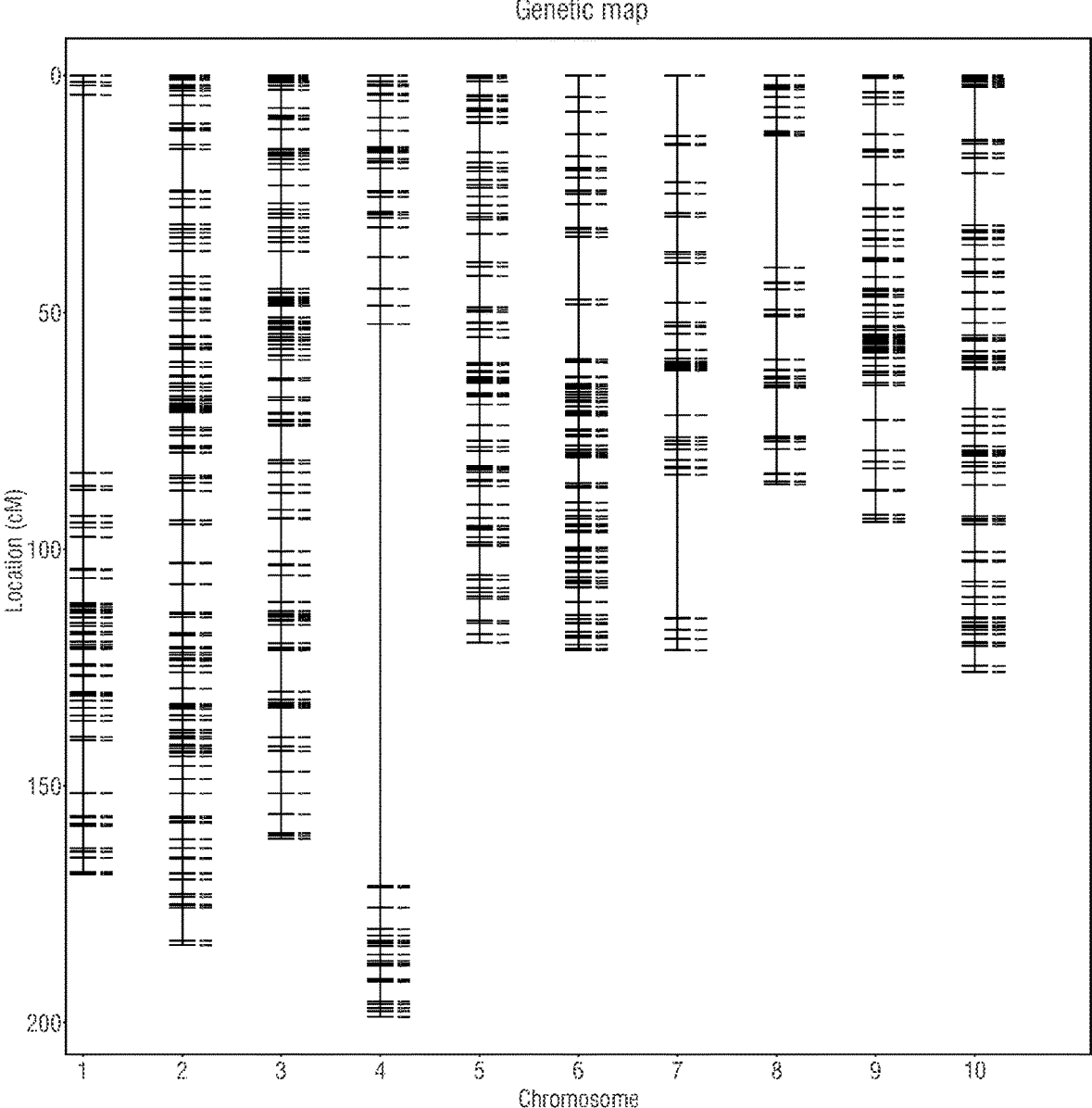

Instead, a revised model for derived chilling sensitivity of US sorghum and inadvertent selection may be more parsimonious (FIG. 4B). Under this model, the African sorghums introduced into the US harbored basal chilling tolerance, but chilling sensitivity was inadvertently selected along with loss-of-function alleles at tan1 and tan2 (from African standing variation), and dw1 and dw3 (from de novo mutations in US). Supporting this revised model, 38 RILs selected for agronomic suitability by the sorghum breeder (R.P.) were fixed for the chilling-susceptibility alleles (at qSbCT09.57 and qSbCT07.59) that are coinherited with desired dw1 and dw3 alleles, respectively (Table 10). Thus, coinheritance of chilling susceptibility with desired traits likely stymied >50 years of chilling tolerance breeding in this crop.

A genotype-to-phenotype modeling approach, which couples genetic and ecophysiological modeling, can help assess the potential value of genotypes in a crop's target population of environments. Preliminary ecophysiological modeling suggests that (were it not for chilling sensitivity) a standard grain sorghum hybrid could escape drought and have higher yields (~5%) if planted 30-60 days early. The improved power and resolution with the chilling NAM provides several new paths to obtain chilling tolerance while bypassing undesirable characteristics from Chinese sorghum. Several chilling tolerance alleles (at qSbCT05.04, qSbCT07.10, qSbCT01.13, and qSbCT01.57) are not coinherited with undesirable alleles for tannins and height (FIG. 3) and can be used directly in marker-assisted introgression. Complementary dominance of Tan1 and non-functional tan2 can be exploited to develop chilling-tolerant sorghums that retain the nontannin phenotype. If the standard model is correct (FIG. 4A), rare recombinants identified with high-density markers will decouple chilling tolerance alleles from undesirable wildtype alleles of tannin and dwarfing genes and bypass undesirable coinheritance. If the revised model is correct (FIG. 4B), antagonistic pleiotropic effects could be bypassed with novel tannin biosynthesis mutations to disrupt tannin production in Tan1 Tan2 chilling-tolerant background and novel dwarfing mutants in Dw1Dw3 chilling-tolerant background.

TABLE 10

| Inadvertent selection of chilling-sensitive alleles | | | | | | |
|---|---|---|---|---|---|---|
| Genotype[a] | EPEC[b] | EPSV1[c] | EPSV2[d] | EPSV3[e] | Height (cm) | Dwarfing alleles[f] |
| 14FS125_Kao | 2.5 | 2.2 | 2.5 | 2.8 | 144 | dw1 dw3 |
| 14FS155_Kao | 2.5 | 1.8 | 2 | 2.1 | 117 | dw1 dw3 |
| 14FS169_Kao | 1.7 | 2.3 | 2.5 | 2.7 | 123 | dw1 dw3 |
| 14FS197_Kao | 2.3 | 2.4 | 2.7 | 3 | 118 | dw1 dw3 |
| 14FS205_Kao | 2.1 | 2.3 | 2.7 | 2.9 | 129 | dw1 dw3 |
| 14FS208_Kao | 3 | 2.6 | 3 | 3.4 | 172 | dw1 dw3 |
| 14FS256_Kao | 1.9 | 2.8 | 3 | 3.1 | 165 | dw1 dw3 |
| 14FS261_Kao | 2.2 | 2.1 | 1.9 | 2.2 | 93 | dw1 dw3 |
| 14FS273_Kao | 2.6 | 2.8 | 2.9 | 3 | 168 | dw1 dw3 |
| 14FS292_Kao | 2 | 2.2 | 2.3 | 2 | 123 | dw1 dw3 |
| 14FS306_Kao | 1.4 | 1.8 | 1.9 | 2.3 | 111 | dw1 dw3 |
| 14FS314_Kao | 2.1 | 2.3 | 2.8 | 2.7 | 119 | dw1 dw3 |
| 14FS336_Kao | 2.5 | 2.2 | 2.5 | 2.7 | 126 | dw1 dw3 |
| 15FS005_NSZ | 2.8 | 2.9 | 3.2 | 3.3 | 168 | dw1 dw3 |
| 15FS032_NSZ | 1.8 | 2.1 | 2.6 | 2.7 | 65 | dw1 dw3 |
| 15FS036_NSZ | 2.4 | 2.4 | 2.5 | 2.7 | 121 | dw1 dw3 |
| 15FS063_NSZ | 2.1 | 2.7 | 2.6 | 3 | 111 | dw1 dw3 |
| 15FS068_NSZ | 2.4 | 2.6 | 2.6 | 3 | 116 | dw1 dw3 |
| 15FS083_NSZ | 3.1 | 2.5 | 2.7 | 3 | 126 | dw1 dw3 |
| 15FS105_NSZ | 2.2 | 2.5 | 2.6 | 2.9 | 116 | dw1 dw3 |
| 15FS142_NSZ | 2 | 2.3 | 2.5 | 2.4 | 115 | dw1 dw3 |
| 15FS152_NSZ | 2 | 2.1 | 2.7 | 2.9 | 115 | dw1 dw3 |
| 15FS202_NSZ | 1.6 | 1.4 | 1.5 | 1.7 | 128 | dw1 dw3 |
| 15FS218_NSZ | 2.9 | 2.7 | 3.1 | 3.4 | 128 | dw1 dw3 |
| 15FS609_HKZa | 2.2 | 2.6 | 2.7 | 2.7 | 97 | dw1 dw3 |
| 15FS642_HKZa | 2.3 | 2.4 | 2.5 | 2.7 | 100 | dw1 dw3 |
| 15FS653_HKZb | 2.2 | 2.3 | 2.9 | 2.8 | 101 | dw1 dw3 |
| 15FS654_HKZa | 1.8 | 2.3 | 2.5 | 2.8 | 109 | dw1 dw3 |
| 15FS666_HKZb | 2.8 | 2.3 | 2.8 | 2.9 | 154 | dw1 dw3 |
| 15FS679_HKZb | 1.5 | 2.2 | 2.3 | 2.9 | 95 | dw1 dw3 |
| 15FS682_HKZa | 1.8 | 2.1 | 2 | 2.7 | 97 | dw1 dw3 |

TABLE 10-continued

| | | | | | | |
|---|---|---|---|---|---|---|
| Genotype[a] | EPEC[b] | EPSV1[c] | EPSV2[d] | EPSV3[e] | Height (cm) | Dwarfing alleles[f] |
| 15FS698_HKZb | 2.9 | 2.9 | 3 | 3.3 | 121 | dw1 dw3 |
| 15FS705_HKZa | 2.7 | 2.7 | 2.5 | 2.8 | 115 | dw1 dw3 |
| 15FS709_HKZb | 2.9 | 2.6 | 2.9 | 3.1 | 122 | dw1 dw3 |
| 15FS715_HKZb | 2.3 | 2.7 | 2.5 | 3.1 | 112 | dw1 dw3 |
| 15FS761_HKZa | 2.4 | 2.7 | 2.7 | 3.2 | 132 | dw1 dw3 |
| 15FS794_HKZa | 2.5 | 3 | 2.8 | 3.1 | 127 | dw1 dw3 |
| 15FS820_HKZb | 2.1 | 2.1 | 2.2 | 2.4 | 97 | dw1 dw3 |
| BTx623_P | 2.5 | 2.6 | 2.7 | 2.9 | 137 | dw1 dw3 |
| HKZ_P | 3.5 | 3.9 | 3.9 | 4.1 | 269 | Dw1 Dw3 |

Inadvertent selection of chilling-sensitive alleles

TABLE 10-continued

| | | | | | | |
|---|---|---|---|---|---|---|
| Genotype[a] | EPEC[b] | EPSV1[c] | EPSV2[d] | EPSV3[e] | Height (cm) | Dwarfing alleles[f] |
| Kao_P | 3.4 | 3.4 | 3.3 | 3.6 | 278 | Dw1 Dw3 |
| NSZ_P | 3.6 | 4 | 3.6 | 3.8 | 246 | Dw1 Dw3 |

Inadvertent selection of chilling-sensitive alleles

[a] The chilling NAM RILs selected based on agronomic suitability.
[b] Early-planted emergence count (EPEC) rating from AB16_b1 field trial.
[c-e] Early-planted seedling vigor (EPSV1-3) rating from AB16_b1 field trial.
[f] Alleles of the Dw1 and Dw3 genes in the selected NAM RILs. The four founders were included as controls.

| SNP_Name | Primer_Name | Variant_Type | Type | Dye | Tail | Primer | Product Size (bp) |
|---|---|---|---|---|---|---|---|
| Sbv3.1_04_60623655S | chill4_1_wt_1 | SNP | WT | Left Fam | GAAGGTGACCAAGTTCATGCT (SEQ ID NO 25) | GCACATCTGCAGCAGTG (SEQ ID NO 26) | |
| | chill4_1_mt_1 | SNP | MT | Left Hex | GAAGGTCGGAGTCAACGGATT (SEQ ID NO 27) | GCACATCTGCAGCAGTC (SEQ ID NO 28) | |
| | chill4_1_com_1 | Complement | | Right | | GTGAAGTGTGCATCCTGAGT (SEQ ID NO 29) | 51 |
| | chill4_1_com_2 | | | | | AAAGTGAAGTGTGCATCCTG (SEQ ID NO 30) | 54 |
| Sbv3.1_04_61096729R | chill4_2_wt_1 | SNP | WT | Left Fam | GAAGGTGACCAAGTTCATGCT (SEQ ID NO 31) | GGCACGCCACCGTCG (SEQ ID NO 32) | |
| | chill4_2_mt_1 | SNP | MT | Left Hex | GAAGGTCGGAGTCAACGGATT (SEQ ID NO 33) | GGCACGCCACCGTCA (SEQ ID NO 34) | |
| | chill4_2_com_1 | Complement | | Right | | CGCCTTCCAGCCATACCAGT (SEQ ID NO 35) | 71 |
| | chill4_2_com_2 | | | | | CTTCCAGCCATACCAGTACGC (SEQ ID NO 36) | 68 |
| Sbv3.1_04_61680898R | chill4_3_wt_1 | SNP | WT | Left Fam | GAAGGTGACCAAGTTCATGCT (SEQ ID NO 37) | GAACAATCCCCGGCCG (SEQ ID NO 38) | |
| | chill4_3_mt_1 | SNP | MT | Left Hex | GAAGGTCGGAGTCAACGGATT (SEQ ID NO 39) | GAACAATCCCCGGCCA (SEQ ID NO 40) | |
| | chill4_3_com_1 | Complement | | Right | | CGCGTCTTGCTAGCTGTTAT (SEQ ID NO 41) | 95 |
| | chill4_3_com_2 | | | | | GCGCGTCTIT-TGCTAGCTGTTA (SEQ ID NO 42) | 96 |
| Sbv3.1_04_62380875W | chill4_4_wt_1 | SNP | WT | Left Fam | GAAGGTGACCAAGTTCATGCT (SEQ ID NO: 43) | CGTTTGGAGAAGATGCAT (SEQ ID NO: 44) | |
| | chill4_4_mt_1 | SNP | MT | Left Hex | GAAGGTCGGAGTCAACGGATT (SEQ ID NO: 45) | CGTTTGGAGAAGATGCAA (SEQ ID NO: 46) | |
| | chill4_4_com_1 | Complement | | Right | | ATGGCAATTGACAAACAGG (SEQ ID NO: 47) | 57 |
| | chill4_4_com_2 | | | | | ACATGGCAATTGACAAACAG (SEQ ID NO: 48) | 59 |
| Sbv3.1_04_62682585R | chill4_5_wt_1 | SNP | WT | Left Fam | GAAGGTGACCAAGTTCATGCT (SEQ ID NO: 49) | TAGCTGCACITTGCCCAA (SEQ ID NO: 50) | |
| | chill4_5_mt_1 | SNP | MT | Left Hex | GAAGGTCGGAGTCAACGGATT (SEQ ID NO: 51) | TAGCTGCACITGCCCAG (SEQ ID NO: 52) | |
| | chill4_5_com_1 | Complement | | Right | | AAATCCGCTAAACAGCCTGA (SEQ ID NO: 53) | 43 |
| | chill4_5_com_2 | | | | | AATCCGCTAAACAGCCTGA (SEQ ID NO: 54) | 42 |

From the above, two varieties were created incorporating the QTLs of the invention into elite germplasm with traits of chilling tolerance, a short plant stature, and a lack of grain tannins. These include KS-090-CT13 (a BC2F4 with QTL from Chromosome 4 and 9) and KS-105-CT124 (a C2LF3 with QTL from chromosomes 1, 2, and 4).

TABLE 12

| Marker Name | Chromosome; position (bp) based on BTx623 reference genome v3.1 | Genomic DNA Sequence (SEQ ID NO: 1-24) SNP site is underlined (position 153) |
|---|---|---|
| S1_5730743 (SEQ ID NO: 1) | 1; 5,730,743 | GCTCTCATCAGGAGGAGAGAGGCCTGAGGAGACCGTGTCTTCTG CTCGTCCTGTCAAATCTATGTCGAAAGATATGGGCTGCTGCGAG CCCAGTTCATGGCGTGCAGCCACCAGCTAGCCAGCATGCCGGCC TCAGGCACATGATCCCGCCCCCATATCTCGTCCCCAGCCAGTCG GCAATGCCTTGCAGCCTGCAGGATCTCTGCTGTGTGCTATCTTG ACCTAGGAGTAGATATATCAGATATCAAACGTCCTTGCTGGGCT CCAGAGCGCGCCTCAAGCCCTCGAGGGAGGAATAATACAA |
| S1_6902771 (SEQ ID NO: 2) | 1; 6,902,771 | GTCCTGTTGATGGTTAGTTTTTGTTTGCTCATAGTGTTGGTAAG GTCTGCCAAATCAGGAACCATGAGTGACAGGCGAGCGCTCACAT GCTCACCTCCAAAAAAATCTCGACTTGCTGCATGAACGTGAGGT TATTTCAGAAGTGAGAATTTCAGAAACGGGTACCGATGTTTCTG TCAGATTTCTGCTGGTTTTGTTCTAGGGCGCGCTGCCAAACTTC ATCATTTAACAGGTTAAAAATAACTGACGTTTGGTGGTTGTTTC GTCGTGTGCAACTGGCACAATCAAATTAGTTTTTGGTCGC |
| S1_9756192 (SEQ ID NO: 3) | 1; 9,756,192 | CCGGCGTTCGGCGTCATCGACACTGCCATCGAGGCCGCCACCGA GTGCTGCTCGCGGGACAAGTACCGGGAAGTGAGGAGCCACCTCG TGGAGATGCTCTGCGATGCCGCGGACAACGACGACGACCTTCGA GCGGAGGGGCTCTGCCGGCTGCTCGACAGGGCCATGGCCGAGGC GCTTCTGACGCTGCAGTCCGTCCCCATCCCGGTGACGCCGACCA TGCTGGCGGCCACCGACGTCGCCAAGACCGTCGGCGGCCTGCTG AGGCACGAGGCCGGGTGGGTGCGCGCCCTCGCGCGCGGCA |
| S1_13188261 (SEQ ID NO: 4) | 1; 13,188,261 | ATGTAGGACAGCGGGACCAGGTCGCCGGACGCGGTGATGGAGCC CCGGAGCGGCAGGCACGGCGTCACGTTGGCGTTGAGCAGCTTGG CGATGGCCTCGAGGATCTCGAAGCGGATGCCCGAGTAGCCCTGG GTGAGGGTGTTGATGCGCACGAGCATGGCCGCACGCGTCACCTC CGCCGGCAGCGTGTAGCCGTCACTGCTGCTGGCTCCAAACACGC CGGCGTTGAGGTATCTTAATATATTTTCAGATCGACGACACATC GTACCCACCCAAATGACGAACGAATTAGCATTATTGCATG |
| S1_13526795 (SEQ ID NO: 5) | 1; 13,526,795 | ACATAATCCTCGACGTTACATGAACCATTATTATTATTTACTGG ATATATATAAATCTATATGTCTGCGTTGAAATCCAGCTAGCCGT ATCTTCGTTGCCAGCTATGCACGTAATTAAAGGAGCAGAGCCCT TAGCTTCTGCATCCGTGAGCTGCGGCGTGTGGCGTCGTGGTGGT TCATGCTCGTCCATCTGCTCCCGGCAACCGGCAGCAGCAGGAGG GGTTCCTGTTTATACCCGGCAGCAAGCAGTACGTCTGGAAGTTA TTACCAGTGTAATTCTTGGACAGGCAGAACTGGTAGCACA |
| S1_57941435 (SEQ ID NO: 6) | 1; 57,941,435 | CCCAGTTTGTTCCCTACTTGATCATGCAGAGCCGCCTGACGAAG CAGGTTCTGCACATCGTCAACCCACTTCTGCTTGCTCGCGTTGC CCTCACACTCGAACTCCACTAGACCTTGCGCCGTGCTAAGGCCG AAGCAGCATGTCTCCTCCGTGGAGTCCTTCCCTGGCTCAGCCCA GGTTGGCAGCTCGCTGTATACACCGTAAACCACGCCTGCACCAG TTACAAGCGAAAGGGTTATTACTGAAATTGAATCTCAAAAACTA CTGGCCAGTTGGACTCAATGTTTCGGTAGTAGAAATCGGA |
| S2_8672301 (SEQ ID NO: 7) | 2; 8,672,301 | TGTTTTTTGACTGTGTAGTAGCTAAACAACTTTGGGCCTTTCTT TCTTAAGTTTTAGATAGACAAGTTGGTATAGACTTTGGGTCTTT AGGAACTATGTGGTTGAGTAACAAGAAGTTCATAGTGGAAAATA CTTTTTGTGTTGCTGCCCTATGGAGGCTTTAGAAACTAAGAAAC AACTTGTGCTTTCTGGGTATACGCTGGATAGATGTGAGGATACT GTTACTGAAGGTAACAACTATGCTGCACAACTGGAGCTCTCTAT GCCCAAAGGAGAAGATACCAGAGTTTCTGGATCGCCTGAA |
| S2_9218398 (SEQ ID NO: 8) | 2; 9,218,398 | ACGTCGTCAAGGTTTTCCGGTGGGATGTTGGGGAGTAGCCCCTG CAGCATTCGCATCATCTGCTCCCTGTAATACATCATCCCGCGTG AGTAGATCGACATCAACCTGATTCCACCCAACTTGACGCTGCCC GGCCTGCCGACGTCGATGACGATGCGCTCAGCGTACTGGTTGCG CCATCCCAAGAGACGCAGCCTCGGCGCACGCAGCGAGAATGATT TGTAGTCTGTGGTGGCTCCAGCTCCACAGTCAATTTCGAACTCT ATCAGCTCCGGTGCGTCGATGGTGATGACTCCGTACGGCG |
| S2_9260382 (SEQ ID NO: 9) | 2; 9,260,382 | GATCCACCGAGGCGCCGTACGGAGTCATCACCATCGACGCACCG GAGCTGATAGAGTTCGAAATTGACTGTGGAGCTGGAGCCACCAC AGACTACAAATCATTCTCGCTGCGTGCGCCGAGGCTGCGTCTCT TGGGATGGCGCAACCAGTACGCTGAGCGCATCGTCATCGACGTC |

TABLE 12-continued

| Marker Name | Chromosome; position (bp) based on BTx623 reference genome v3.1 | Genomic DNA Sequence (SEQ ID NO: 1-24) SNP site is underlined (position 153) |
|---|---|---|
| | | GGCAGGCCGGGCAGCGTCAAGTTGGGTGGAATCAGGTTGATGTC GATCTACTCACGCGGGATGATGTATTACAGGGAGCAGATGATGC GAATGCTGCAGGGGCTACTCCCCAACATCCCACCGGAAAA |
| S4_60623655 (SEQ ID NO: 10) | 4; 60,623,655 | AATAGACAATATTTATACAAAAGTTGTAATAAGACAGATGGTCA AACAAGATGTCTAAAAGTCAACAACAACGGTCTTTTTGAGACGG AGGAAGTATATTTTATTAGTCCTGTGTGGTGATTCAGAACAGAT TTAGGCACATCTGCAGCAGTGCGTGTGGCATCTCAACTCAGGAT GCACACTTCACTTTGAAAAA<u>G</u>CGAATCTGAATTCTGAACATGTA TCTATGTTACATAGGCCATTGGGCTTGCACATGCTGCGATCAAT GCGATCCCGAACTCGCTGTGGCACATAGGAATATGTTTTG |
| S4_61096729 (SEQ ID NO: 11) | 4; 61,096,729 | GGCGCGGGACGGCCGTCCCGGACGTGGCCGTGCTCGCGCGGCAG GGCCTCGCCGTTCATTGTTCGCGAGGGCCGGAGCGGAGCTGCGCG GTCGCGTTCGGGTGGGCTTTGTGGCTGCGGGAACACGCCTAGCT ACGCGTGGCACGCCACCGTCGGCGTGGCCGCAGCCGTGTCCATC GCGGCGTTCGCGTACTGGTA<u>T</u>GGCTGGAAGGCGCCCTACCTGGC GAAGCGCGACTCGTGAACAAGGCAGCAGCCTGGTTCGTGGACCA AGAAGACAACAACTGTACATCAATCAATCGATTAGATCTA |
| S4_61680898 (SEQ ID NO: 12) | 4; 61,680,898 | CTGTTTGCGGACACTGAAACTAAAGCGAAAGCGATCCCCCAACC CCCTTTTCCGCGTGACGTGTGCAAAGTCTACTACGGCAGGGAGA CATGCACGCATTGCCATTGCTTAACAAAGTCGTAGCAGCGGTAA CATAAGAACAATCCCCGGCCGGCATCACGGCATGTGCACGGATG GGGACAGCAGCAGCAGCAGC<u>A</u>GCGAGACCCAACAACATAACAGC TAGCAAGACGCGCCCCTCTCGGACGGACGGAGCTGTTTGTAATT GTGAGGTGGAGTCACAGTCATCAGTCACGCACACACACAT |
| S4_62368531 (SEQ ID NO: 13) | 4; 62,368,531 | GCCGGCGGACGAGTTCTTAGCGAACCTGCCGCCCTCGACGCCGT CGCCGCTTGCCACCGAGTCACCTCGTCGTCCCTTCGCCTTGAGC CGTCTGCACAAGCAGACCAGCAGCAGCATCTGCAGCAGCCAGAG CGCGCCGACGATGCCCAGCCC<u>C</u>GACGGCAAGGCCGGTGACCACCC CGTTCCGGTCGTCGCTCACC<u>A</u>CGGTCGCGTTGGGAGAGGCCGAG GGCGGCGGGGACGCTGGCGTCGTGGAGGCGTTGTTCCGGAGCAC GATTGGGGGCAGCCAATTCGGCACCTGGCGGCGGAGCGGC |
| S4_62380875 (SEQ ID NO: 14) | 4; 62,380,875 | CTGCCTGGCTGCCTGAGAGGCAAGGCGCATCCGTAAAATACGCC GGCCTAGCGCTGGACAGCGACTGACTACTGGCACATGGCAGGCG TCAGCCGAGCCGCGGGTCCCAAGTAGCTGCAGCGAACATTCGTT TGGCGTTTGGAGAAGATGCATGGGTGATACGATCCTCTTGGCCT GTTTGTCAATTGCCATGTAG<u>G</u>ACGAAGATAAAGATAAACAAAGC GACAGACTAGTAATAAGCTCTAGCAGTAGAAGCTACCTCCATCA TTCGTGCTGCTCACTCAGCTCAGCTCGTTATAATAACGCA |
| S4_62455479 (SEQ ID NO: 15) | 4; 62,455,479 | CATATCGGGTGATTTTGGTAATGAAATTGCGAGGGTTGGAGAGA TCCGATGAAATAGGCATCCTTACACGAAGGGTGCATACATTCTC GTAGTTCTTGAGCAGCTCCTCAACCTATAAAAATAACTGTTAGG TTCACATGGAAGGAATAAATGTTCCACCATCCAATCAGATACAG CAGCATGAAATACAAAAGGT<u>A</u>AAAAAAAAATGTCACATGCCAGCA TTACTACAAAAATGTTTGACCAGAACAGCTTAGTTTCTCTGAAA ACATCAGTGTGTGGAACTGCGGATACAATGGTAACTTTTG |
| S4_62682585 (SEQ ID NO: 16) | 4: 62,682,585 | TCTGTAGAAACTATTGATGAGTGCGAATCCAGGAAGCTTGATGA TTTTTCACTTTGAAGGCAGTATCGTAGCTTGTTAGGTGTGCATG ACAGCCCGTGCTCTATTCTTTGAAGATTGGTCAAATTTGAAAAA CTTGTAGCTGCACTTGCCCAA<u>C</u>TAGAATCAGGCTGTTTAGCGGA TTTGAATTGTTGAGCACTTT<u>C</u>TGAAATAATATTGTGCAGCAAAT TGCTGTCACTTTGAAATACTTTAAGAGTACTTATTGACTTGGAG TTCACTGGCATGGCCACTATGTGAGGATTCAGACCACTGA |
| S5_4284787 (SEQ ID NO: 17) | 5; 4,284,787 | CGGCACTCGCCGGCCGCAGAGGATCCCGAGGGATTCGGTGGGGA GGCCCCACCACCCGTCGCCGTCGCGGGACCCGGTGGGGAGGCGC GCGCGGAAAAGGTCAAGGGGTCGCCCAACCGGCGCTCGGCAGCT CGGCGCCACGTCGCTGTCGGCGGTGGGCAGCCGATGGGCCCCG CCGGCCACTTTCCCACGTTGG<u>C</u>TGCCCGGCCCGCAAGGAATATG TTAGTGCGGGGCCCGCGGAGGGGAACCGGCCGCGTGGAGCCTGT CGTCCAGTCGCCTCGTCCTAGTAGTCCTAGCTACTAGTCC |
| S5_4403613 (SEQ ID NO: 18) | 5; 4,403,613 | GCACTAGAAGCATCAATTTTGAGGAATGAGGTATGCTGCATAAT CCATTCACAGCTTTACGACGTTCTTGCTGTTCATTGGGACTCGA TATATTCAATATGTACTGATCCTGCGATCATCCTGAAGCTAATA TCATATTTCTGGATCTTTGT<u>C</u>AAATAAATAAGGGTTCATGGTCT GGCTCTGAATCCTCAGCTTC<u>C</u>GAAAGATCGCTGCCATTCCTAGC |

TABLE 12-continued

| Marker Name | Chromosome; position (bp) based on BTx623 reference genome v3.1 | Genomic DNA Sequence (SEQ ID NO: 1-24) SNP site is underlined (position 153) |
| --- | --- | --- |
| | | ACAGGATTGTGAAACAGATATTGACACAAGACTTCTTAAGATTG TAAAGAAGGTTGCTTCTGGATCTTGTGGGGACATGTGAGT |
| S7_8916696 (SEQ ID NO: 19) | 7; 8,916,696 | AAGAAATAAAAATATCAGTCAAATCGACGTCGTGGTGAGAAAAA AGAGAGGGAAAAACAAAAGAAACGCAGCGCGAGGGAATATTGTG TGCAGTGCAGGTACGTACTACCAGGTAGCGTGGCGGTGGCGGCG GCTGCGAGTGGCCCCCCACCTCACCCAGACGCGCGCGGACGGAA CGGCGCCGCGGATCGTGTGGACTTTTTTAAAAACCGGGGGAGCG GCGGTTGGTGGCGACGTCGTCGGCGGCACGCGGCAGGCGCATCG CGGGGAGCAGCCGTCACGCCGCTGTCAGGGGGTTGGACGG |
| S7_12580350 (SEQ ID NO: 20) | 7; 12,580,350 | GGCTCCGGCACCGGCACGCCGCCGTCGCCAGCACCGATGTTCGC AACGGGGGCGGCCGTGTATGATCCCACTGCCCCCAACGGCACCA TGTATGGGCTGCTGCAGTGCATGAGGGACCGGACGGCGGCGGAG TGCGCCAAGTGCTTGAATGACTCGGTGCAGCAGCTGCCGTCGTG CTGCCGTGGTCACAGGGGCGGGATTGTGATGGGCTACAACTGCT ACCTGCGCATGGAGGTGTACCCCTACTATGATCTGGCCCTAGAT GGGCCACCGCTTGTTCTAGCTCCAGCTCCAGCTCCAGCTC |
| S7_59290017 (SEQ ID NO: 21) | 7; 59,290,017 | GCGGAAACCTAGCTAGTATATTCTACGGATCGAGTACGTGTATA ATAGCTTGGGATGGGCCAGAAACCTTGTTTTTTTACTTGGTTGA TTGCTGGCTGCTGCTTGCCGCTTTCGCTTGCGATCGAGTTGTGA GTGCGATGAGGCACGCGGGGACGCGCTGGCCGCTGCCGATTGGC CGCCGGCCGGGCGCCATGCCCGCCGGCGGCTACGCATAGTGGTC CGTAGCCGTCGGCGGATAGAGATGGACGTCGTCGTATACAGCAT GTGCAGCGTAGCGGTACGCCGAGCGGCGGCCGACGAGGAA |
| S7_59915577 (SEQ ID NO: 22) | 7; 59,915,577 | GACGCACAGGGAGGAGCACGACGCGTCCTCGTCCTTCTCCCACC TCCAGCCGCCGTCTGTCGACAGCGGGAACTTGAGAGTCCACGTC GTGAGCGCCACCGTCACCTCCTCGCCGCCGTCCATGCATACGAG CTTGATGGTCTCCGTGTCCAAGCAGCGCACGGAACGGTACTCCG TCGAGTCAAAAGGTCTGTGGCCGCATACCACGGGCAACGGGATG AAGGTGAACACCAAGCCGTCCTCCTCGTCGTCGTCGTCGTCGTC GTCGCCGGCGGCCGTGCCGGCGGTGCTGCTGCTGATGTTG |
| S9_55625332 (SEQ ID NO: 23) | 9; 55,625,332 | TTTAGAATAAGATTAGTTCACATTATATTGTCCTCTTATTCACG TGCTGTCCATCCTGAATTCCTGATCCTCCATCATAACCAAGTAG TCACTCCACCATAGAATCAAAGAGCAGCGGAGCTCTGCCAAGCA TGTCTTAATGTGGTGGTATCATTGATCATTATATTTTAGGAAAA TGACATGCTATCAGTAGTATTATCGATGATGTTTGTGTTGCTTG ATGTTGCAGCAAGTGCCTCCTCTTCATTTTAATTCAGTATGTCT CATGCGCCCCTGCTCTGACATGATCTTTTTGTTCCTGTTG |
| S9_58070153 (SEQ ID NO: 24) | 9; 58,070,153 | TGCACACAGCCACACAGGCCAAGGTTTTTGGCATGGCACAAGGC CGGCCAATGCCCATGCGCCATGACTCGAGCTGCTGCTGCTGTCG GTTTCTGGTGGTGGCCTATGCTGCGCCACGCGCCCTACTCTGGT GCGGCGGCGTTCGTGTTCGAGTGGGTAGCAGCCTCTGCAGTCTT GCTAGTCCAAGCTGGCCTGTAAAGTGTCAGGAGCTTGTTCTGCG CCATGAATAGACATAAATATCCGGCTGAAGGCTGCCTGCAGTGT CCATGCCTCGATCGGACACGCTGCCCGCCGGCGCCGGCCC |

Deposits

Applicant(s) will make a deposit of at least 625 seeds of Chilling Tolerant Sorghum lines KS-090-CT13 and KS-105-CT124, with the American Type Culture Collection (ATCC), Manassas, VA 20110 USA, ATCC Deposit No. _____. The seeds deposited with the ATCC on _____ will be taken from the deposit maintained by Kansas State University, 1712 Claflin Road Manhattan, KS 66506 since prior to the filing date of this application. Access to this deposit will be available during the pendency of the application to the Commissioner of Patents and Trademarks and persons determined by the Commissioner to be entitled thereto upon request. Upon issue of claims, the Applicant(s) will make available to the public, pursuant to 37 CFR 1.808, a deposit of at least 2500 seeds of sorghum cultivar KS-090-CT13 and KS-105-CT124 with the American type Culture Collection (ATCC), 10801 University Boulevard, Manassas, VA 20110-

2209. This deposit of sorghum cultivars KS-090-CT13 and KS-105-CT124 will be maintained in the ATCC depository, which is a public depository, for a period of 30 years, or 5 years after the most recent request, or for the enforceable life of the patent, whichever is longer, and will be replaced if it becomes nonviable during that period. Additionally, Applicants have or will satisfy all the requirements of 37 C.F.R. §§ 1.801-1.809, including providing an indication of the viability of the sample. Applicants have no authority to waive any restrictions imposed by law on the transfer of biological material or its transportation in commerce. Applicants do not waive any infringement of their rights granted under this patent or under the Plant Variety Protection Act (7 USC 2321 et seq.).

Applicant reserves the right to claim the following:

a. A sorghum variety with chilling tolerance, a short stature, and a lack of grain tannins.

b. The sorghum variety of claim a wherein said chilling tolerance plant tolerance at temperatures of from about 1 to about 18° C.

c. The sorghum variety of claim 1 wherein said plant stature is less than about 2 m.

d. The sorghum variety of claim a wherein plant height is conferred other than d1 or d3.

e. The sorghum variety of claim a wherein tan 1 or tan 2 has been deactivated f. The sorghum plant of claim a, wherein the plant comprises one or more chilling tolerance QTL in its genome, wherein the QTL is one or more of qSbCT01.06, qSbCT01.13, qSbCT01.57, qSbCT02.08, qSbCT04.62, qSbCT05.04, qSbCT07.10, qSbCT07.59, and qSbCT09.57.

g. The sorghum plant of claim b, wherein the plant comprises qSbCT01.06, qSbCT01.13, qSbCT02.08, qSbCT04.62, and qSbCT09.57 in its gen h. A plant part of the plant variety of claim a.

i. The sorghum plant of claim a, wherein the chilling tolerance is derived from Sorghum cultivar KS-090-CT13 or KS-105-CT124, wherein a representative sample of seed of said cultivar was deposited under ATCC Accession No. PTA-_____.

j. The sorghum variety of claim a, wherein the chilling tolerance is derived from Sorghum cultivar Hong Ke Zi, Kaoliang, or Niu Sheng Zui.

k. The sorghum plant of claim a, wherein the variety is an elite line.

l. A sorghum plant from an elite sorghum variety comprising in its genome at least one introgressed locus associated with chilling tolerance, wherein the locus is one or more of qSbCT01.06, qSbCT01.13, qSbCT01.57, qSbCT02.08, qSbCT04.62, qSbCT05.04, qSbCT07.10, qSbCT07.59, and qSbCT09.57.

m. A sorghum plant of claim 1, wherein the plant has a short stature and lacks grain tannins.

n. A part of the sorghum plant or plant variety of any one of claims a-m, wherein the part is pollen, an ovule, a leaf, an embryo, a root, a root tip, an anther, a flower, a stem, a shoot, a seed, a protoplast, a cell, or a callus.

o. The part of the sorghum plant of claim h, wherein the part is a seed.

p. A plant of sorghum cultivar KS-090-CT13 or KS-105-CT124, wherein representative seed of said cultivar has been deposited under ATCC Accession No. PTA-_____.

q. An elite sorghum variety adapted to the growing region of the United States with chilling tolerance.

r. A method of identifying genetic markers associated with chilling tolerance in a cereal plant, comprising screening said plant for makers analogous to those in KS-090-CT13 or KS-105-CT124.

---

---

What is claimed is:

1. A method of introgressing a chilling tolerance locus into a chilling sensitive sorghum plant, the method comprising:

providing a first sorghum plant with a chilling tolerance locus wherein the locus is on chromosome 1 and linked to a single nucleotide polymorphism (SNP) corresponding to nucleic acid position 153 of SEQ ID NO: 3, SEQ ID NO: 4, and SEQ ID NO: 5, wherein the first sorghum plant is Sorghum cultivar Hong Ke Zi, Kaoliang, or Niu Sheng Zui or has Sorghum cultivar Hong Ke Zi, Kaoliang, or Niu Sheng Zui as an ancestor;

providing a second sorghum plant;

crossing the first sorghum plant with the second sorghum plant to produce a population of sorghum progeny plants;

selecting from said population at least one sorghum plant having the chilling tolerance locus by marker assisted selection.

2. A method of introgressing a chilling tolerance locus into a chilling sensitive sorghum plant, the method comprising:

providing a first sorghum plant with a chilling tolerance locus wherein the locus is on chromosome 1 and linked to a single nucleotide polymorphism (SNP) corresponding to nucleic acid position 153 of SEQ ID NO: 3, SEQ ID NO: 4, and SEQ ID NO: 5, wherein the first sorghum plant is Sorghum cultivar Hong Ke Zi, Kaoliang, or Niu Sheng Zui or has Sorghum cultivar Hong Ke Zi, Kaoliang, or Niu Sheng Zui as an ancestor;

providing a second sorghum plant, wherein the second sorghum plant is Sorghum cultivar BTx623;

crossing the first sorghum plant with the second sorghum plant to produce a population of sorghum progeny plants;

selecting from said population at least one sorghum plant having the chilling tolerance locus.

* * * * *

SEQUENCE LISTING

```
<160> NUMBER OF SEQ ID NOS: 54

<210> SEQ ID NO 1
<211> LENGTH: 304
<212> TYPE: DNA
<213> ORGANISM: Sorghum bicolor

<400> SEQUENCE: 1
gctctcatca ggaggagaga ggcctgagga gaccgtgtct tctgctcgtc ctgtcaaatc      60
tatgtcgaaa gatatgggct gctgcgagcc cagttcatgg cgtgcagcca ccagctagcc     120
agcatgccgg cctcaggcac atgatcccgc ccccatatct cgtcccagc cagtcggcaa      180 tgccttgcag cctgcaggat ctctgctgtg tgctatcttg acctaggagt agatatatca     240
gatatcaaac gtccttgctg ggctccagag cgcgcctcaa gccctcgagg gaggaataat     300
acaa                                                                  304

<210> SEQ ID NO 2
<211> LENGTH: 304
<212> TYPE: DNA
<213> ORGANISM: Sorghum bicolor

<400> SEQUENCE: 2
gtcctgttga tggttagttt ttgtttgctc atagtgttgg taaggtctgc caaatcagga      60
accatgagtg acaggcgagc gctcacatgc tcacctccaa aaaaatctcg acttgctgca     120
tgaacgtgag gttatttcag aagtgagaat ttcagaaacg ggtaccgatg tttctgtcag     180
atttctgctg gttttgttct agggcgcgct gccaaacttc atcatttaac aggttaaaaa     240
taactgacgt ttggtggttg tttcgtcgtg tgcaactggc acaatcaaat tagtttttgg     300
tcgc                                                                  304

<210> SEQ ID NO 3
<211> LENGTH: 304
<212> TYPE: DNA
```

```
<213> ORGANISM: Sorghum bicolor

<400> SEQUENCE: 3
ccggcgttcg gcgtcatcga cactgccatc gaggccgcca ccgagtgctg ctcgcgggac      60
aagtaccggg aagtgaggag ccacctcgtg gagatgctct gcgatgccgc ggacaacgac     120
gacgaccttc gagcggaggg gctctgccgg ctgctcgaca gggccatggc cgaggcgctt     180
ctgacgctgc agtccgtccc catcccggtg acgccgacca tgctggcggc caccgacgtc     240
gccaagaccg tcggcggcct gctgaggcac gaggccgggt gggtgcgcgc cctcgcgcgc     300
ggca                                                                 304

<210> SEQ ID NO 4
<211> LENGTH: 304
<212> TYPE: DNA
<213> ORGANISM: Sorghum bicolor

<400> SEQUENCE: 4
atgtaggaca gcgggaccag gtcgccggac gcggtgatgg agccccggag cggcaggcac      60
ggcgtcacgt tggcgttgag cagcttggcg atggcctcga ggatctcgaa gcggatgccc     120
gagtagccct gggtgagggt gttgatgcgc acgagcatgc ccgcacgcgt cacctccgcc     180
ggcagcgtgt agccgtcact gctgctggct ccaaacacgc cggcgttgag gtatcttaat     240
atattttcag atcgacgaca catcgtaccc acccaaatga cgaacgaatt agcattattg     300
catg                                                                 304

<210> SEQ ID NO 5
<211> LENGTH: 304
<212> TYPE: DNA
<213> ORGANISM: Sorghum bicolor

<400> SEQUENCE: 5
acataatcct cgacgttaca tgaaccatta ttattattta ctggatatat ataaatctat      60
atgtctgcgt tgaaatccag ctagccgtat cttcgttgcc agctatgcac gtaattaaag     120
gagcagagcc cttagcttct gcatccgtga gctgcggcgt gtggcgtcgt ggtggttcat     180
gctcgtccat ctgctcccgg caaccggcag cagcaggagg ggttcctgtt tatacccggc     240
agcaagcagt acgtctggaa gttattacca gtgtaattct tggacaggca gaactggtag     300
caca                                                                 304

<210> SEQ ID NO 6
<211> LENGTH: 304
<212> TYPE: DNA
<213> ORGANISM: Sorghum bicolor

<400> SEQUENCE: 6
cccagtttgt tccctacttg atcatgcaga gccgcctgac gaagcaggtt ctgcacatcg      60
tcaacccact tctgcttgct cgcgttgccc tcacactcga actccactag accttgcgcc     120
gtgctaaggc cgaagcagca tgtctcctcc gtggagtcct tccctggctc agcccaggtt     180
ggcagctcgc tgtatacacc gtaaaccacg cctgcaccag ttacaagcga aagggttatt     240
actgaaattg aatctcaaaa actactggcc agttggactc aatgtttcgg tagtagaaat     300
cgga                                                                 304

<210> SEQ ID NO 7
<211> LENGTH: 304
```

-continued

```
<212> TYPE: DNA
<213> ORGANISM: Sorghum bicolor

<400> SEQUENCE: 7
tgttttttga ctgtgtagta gctaaacaac tttgggcctt tctttcttaa gttttagata      60
gacaagttgg tatagacttt gggtctttag gaactatgtg gttgagtaac aagaagttca     120
tagtggaaaa tactttttgt gttgctgccc tatggaggct ttagaaacta agaaacaact     180
tgtgctttct gggtatacgc tggatagatg tgaggatact gttactgaag gtaacaacta     240
tgctgcacaa ctggagctct ctatgcccaa aggagaagat accagagttt ctggatcgcc     300
tgaa                                                                    304

<210> SEQ ID NO 8
<211> LENGTH: 304
<212> TYPE: DNA
<213> ORGANISM: Sorghum bicolor

<400> SEQUENCE: 8
acgtcgtcaa ggttttccgg tgggatgttg gggagtagcc cctgcagcat tcgcatcatc      60
tgctccctgt aatacatcat cccgcgtgag tagatcgaca tcaacctgat tccacccaac     120
ttgacgctgc ccggcctgcc gacgtcgatg acgatgcgct cagcgtactg gttgcgccat     180
cccaagagac gcagcctcgg cgcacgcagc gagaatgatt tgtagtctgt ggtggctcca     240
gctccacagt caatttcgaa ctctatcagc tccggtgcgt cgatggtgat gactccgtac     300
ggcg                                                                    304

<210> SEQ ID NO 9
<211> LENGTH: 304
<212> TYPE: DNA
<213> ORGANISM: Sorghum bicolor

<400> SEQUENCE: 9
gatccaccga ggcgccgtac ggagtcatca ccatcgacgc accggagctg atagagttcg      60
aaattgactg tggagctgga gccaccacag actacaaatc attctcgctg cgtgcgccga     120
ggctgcgtct cttgggatgg cgcaaccagt acgctgagcg catcgtcatc gacgtcggca     180
ggccgggcag cgtcaagttg ggtggaatca ggttgatgtc gatctactca cgcgggatga     240
tgtattacag ggagcagatg atgcgaatgc tgcaggggct actccccaac atcccaccgg     300
aaaa                                                                    304

<210> SEQ ID NO 10
<211> LENGTH: 304
<212> TYPE: DNA
<213> ORGANISM: Sorghum bicolor

<400> SEQUENCE: 10
aatagacaat atttatacaa aagttgtaat aagacagatg gtcaaacaag atgtctaaaa      60
gtcaacaaca acggtctttt tgagacggag gaagtatatt ttattagtcc tgtgtggtga     120
ttcagaacag atttaggcac atctgcagca gtgcgtgtgg catctcaact caggatgcac     180
acttcacttt gaaaaagcga atctgaattc tgaacatgta tctatgttac ataggccatt     240
gggcttgcac atgctgcgat caatgcgatc ccgaactcgc tgtggcacat aggaatatgt     300
tttg                                                                    304

<210> SEQ ID NO 11
```

```
<211> LENGTH: 304
<212> TYPE: DNA
<213> ORGANISM: Sorghum bicolor

<400> SEQUENCE: 11
ggcgcgggac ggccgtcccg gacgtggccg tgctcgcgcg gcagggcctc gcgttcattg      60
ttcgcgaggg ccggagcgga gctgcgcggt cgcgttcggg tgggctttgt ggctgcggga     120
acacgcctag ctacgcgtgg cacgccaccg tcggcgtggc cgcagccgtg tccatcgcgg     180
cgttcgcgta ctggtatggc tggaaggcgc cctacctggc gaagcgcgac tcgtgaacaa     240
ggcagcagcc tggttcgtgg accaagaaga caacaactgt acatcaatca atcgattaga     300
tcta                                                                  304

<210> SEQ ID NO 12
<211> LENGTH: 304
<212> TYPE: DNA
<213> ORGANISM: Sorghum bicolor

<400> SEQUENCE: 12
ctgtttgcgg acactgaaac taaagcgaaa gcgatccccc aaccccnnnt tccgcgtgac      60
gtgtgcaaag tctactacgg cagggagaca tgcacgcatt gccattgctt aacaaagtcg     120
tagcagcggt aacataagaa caatccccgg ccggcatcac ggcatgtgca cggatgggga     180
cagcagcagc agcagcagcg agacccaaca acataacagc tagcaagacg cgcccctctc     240
ggacggacgg agctgtttgt aattgtgagg tggagtcaca gtcatcagtc acgcacacac     300
acat                                                                  304

<210> SEQ ID NO 13
<211> LENGTH: 304
<212> TYPE: DNA
<213> ORGANISM: Sorghum bicolor

<400> SEQUENCE: 13
gccggcggac gagttcttag cgaacctgcc gccctcgacg ccgtcgccgc ttgccaccga      60
gtcacctcgt cgtcccttcg ccttgagccg tctgcacaag cagaccagca gcagcatctg     120
cagcagccag agcgcgccga cgatgcccag cccgacggca aggccggtga ccaccccgtt     180
ccggtcgtcg ctcaccacgg tcgcgttggg agaggccgag ggcggcgggg acgctggcgt     240
cgtggaggcg ttgttccgga gcacgattgg gggcagccaa ttcggcacct ggcggcggag     300
cggc                                                                  304

<210> SEQ ID NO 14
<211> LENGTH: 304
<212> TYPE: DNA
<213> ORGANISM: Sorghum bicolor

<400> SEQUENCE: 14
ctgcctggct gcctgagagg caaggcgcat ccgtaaaata cgccggccta gcgctggaca      60
gcgactgact actggcacat ggcaggcgtc agccgagccg cgggtcccaa gtagctgcag     120
cgaacattcg tttggcgttt ggagaagatg catgggtgat acgatcctct tggcctgttt     180
gtcaattgcc atgtaggacg aagataaaga taaacaaagc gacagactag taataagctc     240
tagcagtaga agctacctcc atcattcgtg ctgctcactc agctcagctc gttataataa     300
cgca                                                                  304
```

-continued

```
<210> SEQ ID NO 15
<211> LENGTH: 304
<212> TYPE: DNA
<213> ORGANISM: Sorghum bicolor

<400> SEQUENCE: 15
catatcgggt gattttggta atgaaattgc gagggttgga gagatccgat gaaataggca      60
tccttacacg aagggtgcat acattctcgt agttcttgag cagctcctca acctataaaa     120
ataactgtta ggttcacatg gaaggaataa atgttccacc atccaatcag atacagcagc     180
atgaaataca aaaggtaaaa aaaaatgtca catgccagca ttactacaaa aatgtttgac     240
cagaacagct tagtttctct gaaaacatca gtgtgtggaa ctgcggatac aatggtaact     300
tttg                                                                  304

<210> SEQ ID NO 16
<211> LENGTH: 304
<212> TYPE: DNA
<213> ORGANISM: Sorghum bicolor

<400> SEQUENCE: 16
tctgtagaaa ctattgatga gtgcgaatcc aggaagcttg atgatttttc actttgaagg      60
cagtatcgta gcttgttagg tgtgcatgac agcccgtgct ctattctttg aagattggtc     120
aaatttgaaa aacttgtagc tgcacttgcc caactagaat caggctgttt agcggatttg     180
aattgttgag cactttctga ataatatattg tgcagcaaat tgctgtcact ttgaaatact     240
ttaagagtac ttattgactt ggagttcact ggcatggcca ctatgtgagg attcagacca     300
ctga                                                                  304

<210> SEQ ID NO 17
<211> LENGTH: 304
<212> TYPE: DNA
<213> ORGANISM: Sorghum bicolor

<400> SEQUENCE: 17
cggcactcgc cggccgcaga ggatcccgag ggattcggtg gggaggcccc accaccgtc       60 gccgtcgcgg gacccggtgg ggaggcgcgc gcggaaaagg tcaaggggtc gcccaaccgg     120
cgctcggcag ctcggcgcca cgtcgctgtc ggcggtgggc cagccgatgg gccccgccgg     180
ccactttccc acgttggctg cccggcccgc aaggaatatg ttagtgcggg gcccgcggag     240
gggaaccggc cgcgtggagc ctgtcgtcca gtcgcctcgt cctagtagtc ctagctacta     300
gtcc                                                                  304

<210> SEQ ID NO 18
<211> LENGTH: 304
<212> TYPE: DNA
<213> ORGANISM: Sorghum bicolor

<400> SEQUENCE: 18
gcactagaag catcaatttt gaggaatgag gtatgctgca taatccattc acagctttac      60
gacgttcttg ctgttcattg ggactcgata tattcaatat gtactgatcc tgcgatcatc     120
ctgaagctaa tatcatattt ctggatcttt gtcaaataaa taagggttca tggtctggct     180
ctgaatcctc agcttccgaa agatcgctgc cattcctagc acaggattgt gaaacagata     240
ttgacacaag acttcttaag attgtaaaga aggttgcttc tggatcttgt ggggacatgt     300
gagt                                                                  304
```

-continued

```
<210> SEQ ID NO 19
<211> LENGTH: 304
<212> TYPE: DNA
<213> ORGANISM: Sorghum bicolor

<400> SEQUENCE: 19
aagaaataaa aatatcagtc aaatcgacgt cgtggtgaga aaaagagag ggaaaaacaa        60 aagaaacgca gcgcgaggga atattgtgtg cagtgcaggt acgtactacc aggtagcgtg       120
gcggtggcgg cggctgcgag tggcccccca cctcacccag acgcgcgcgg acggaacggc       180
gccgcggatc gtgtggactt ttttaaaaac cggggagcg gcggttggtg gcgacgtcgt        240
cggcggcacg cggcaggcgc atcgcgggga gcagccgtca cgccgctgtc aggggggttgg      300 acgg                                                                    304

<210> SEQ ID NO 20
<211> LENGTH: 304
<212> TYPE: DNA
<213> ORGANISM: Sorghum bicolor

<400> SEQUENCE: 20
ggctccggca ccggcacgcc gccgtcgcca gcaccgatgt tcgcaacggg ggcggccgtg        60
tatgatccca ctgcccccaa cggcaccatg tatgggctgc tgcagtgcat gagggaccgg       120
acggcggcgg agtgcgccaa gtgcttgaat gactcggtgc agcagctgcc gtcgtgctgc       180
cgtggtcaca ggggcgggat tgtgatgggc tacaactgct acctgcgcat ggaggtgtac       240
ccctactatg atctggccct agatgggcca ccgcttgttc tagctccagc tccagctcca       300
gctc                                                                    304

<210> SEQ ID NO 21
<211> LENGTH: 304
<212> TYPE: DNA
<213> ORGANISM: Sorghum bicolor

<400> SEQUENCE: 21
gcggaaacct agctagtata ttctacggat cgagtacgtg tataatagct tgggatgggc        60
cagaaacctt gttttttttac ttggttgatt gctggctgct gcttgccgct ttcgcttgcg      120
atcgagttgt gagtgcgatg aggcacgcgg ggacgcgctg gccgctgccg attggccgcc       180
ggccgggcgc catgcccgcc ggcggctacg catagtggtc cgtagccgtc ggcggataga       240
gatggacgtc gtcgtataca gcatgtgcag cgtagcggta cgccgagcgg cggccgacga       300
ggaa                                                                    304

<210> SEQ ID NO 22
<211> LENGTH: 304
<212> TYPE: DNA
<213> ORGANISM: Sorghum bicolor

<400> SEQUENCE: 22
gacgcacagg gaggagcacg acgcgtcctc gtccttctcc cacctccagc cgccgtctgt        60
cgacagcggg aacttgagag tccacgtcgt gagcgccacc gtcacctcct cgccgccgtc       120
catgcatacg agcttgatgg tctccgtgtc caagcagcgc acggaacggt actccgtcga       180
gtcaaaaggt ctgtggccgc ataccacggg caacgggatg aaggtgaaca ccaagccgtc       240
ctcctcgtcg tcgtcgtcgt cgtcgtcgcc ggcggccgtg ccggcggtgc tgctgctgat       300
gttg                                                                    304
```

```
<210> SEQ ID NO 23
<211> LENGTH: 304
<212> TYPE: DNA
<213> ORGANISM: Sorghum bicolor

<400> SEQUENCE: 23
tttagaataa gattagttca cattatattg tcctcttatt cacgtgctgt ccatcctgaa      60
ttcctgatcc tccatcataa ccaagtagtc actccaccat agaatcaaag agcagcggag     120
ctctgccaag catgtcttaa tgtggtggta tcattgatca ttatatttta ggaaaatgac     180
atgctatcag tagtattatc gatgatgttt gtgttgcttg atgttgcagc aagtgcctcc     240
tcttcatttt aattcagtat gtctcatgcg cccctgctct gacatgatct ttttgttcct     300
gttg                                                                   304

<210> SEQ ID NO 24
<211> LENGTH: 304
<212> TYPE: DNA
<213> ORGANISM: Sorghum bicolor

<400> SEQUENCE: 24
tgcacacagc cacacaggcc aaggtttttg gcatggcaca aggccggcca atgcccatgc      60
gccatgactc gagctgctgc tgctgtcggt ttctggtggt ggcctatgct cgcgccacgcg   120 ccctactctg gtgcggcggc gttcgtgttc gagtgggtag cagcctctgc agtcttgcta     180
gtccaagctg gcctgtaaag tgtcaggagc ttgttctgcg ccatgaatag acataaatat     240
ccggctgaag gctgcctgca gtgtccatgc ctcgatcgga cacgctgccc gccggcgccg     300
gccc                                                                   304

<210> SEQ ID NO 25
<211> LENGTH: 21
<212> TYPE: DNA
<213> ORGANISM: Artificial Sequence
<220> FEATURE:
<223> OTHER INFORMATION: Primer

<400> SEQUENCE: 25
gaaggtgacc aagttcatgc t                                                 21

<210> SEQ ID NO 26
<211> LENGTH: 17
<212> TYPE: DNA
<213> ORGANISM: Artificial Sequence
<220> FEATURE:
<223> OTHER INFORMATION: Primer

<400> SEQUENCE: 26
gcacatctgc agcagtg                                                      17

<210> SEQ ID NO 27
<211> LENGTH: 21
<212> TYPE: DNA
<213> ORGANISM: Artificial Sequence
<220> FEATURE:
<223> OTHER INFORMATION: Primer

<400> SEQUENCE: 27
gaaggtcgga gtcaacggat t                                                 21

<210> SEQ ID NO 28
```

```
<211> LENGTH: 17
<212> TYPE: DNA
<213> ORGANISM: Artificial Sequence
<220> FEATURE:
<223> OTHER INFORMATION: Primer

<400> SEQUENCE: 28
gcacatctgc agcagtc                                                  17

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
gtgaagtgtg catcctgagt                                               20

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
aaagtgaagt gtgcatcctg                                               20

<210> SEQ ID NO 31
<211> LENGTH: 21
<212> TYPE: DNA
<213> ORGANISM: Artificial Sequence
<220> FEATURE:
<223> OTHER INFORMATION: Primer

<400> SEQUENCE: 31
gaaggtgacc aagttcatgc t                                             21

<210> SEQ ID NO 32
<211> LENGTH: 15
<212> TYPE: DNA
<213> ORGANISM: Artificial Sequence
<220> FEATURE:
<223> OTHER INFORMATION: Primer

<400> SEQUENCE: 32
ggcacgccac cgtcg                                                    15

<210> SEQ ID NO 33
<211> LENGTH: 21
<212> TYPE: DNA
<213> ORGANISM: Artificial Sequence
<220> FEATURE:
<223> OTHER INFORMATION: Primer

<400> SEQUENCE: 33
gaaggtcgga gtcaacggat t                                             21

<210> SEQ ID NO 34
<211> LENGTH: 15
<212> TYPE: DNA
<213> ORGANISM: Artificial Sequence
<220> FEATURE:
<223> OTHER INFORMATION: Primer

<400> SEQUENCE: 34
```

```
ggcacgccac cgtca                                                    15

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
cgccttccag ccataccagt                                               20

<210> SEQ ID NO 36
<211> LENGTH: 21
<212> TYPE: DNA
<213> ORGANISM: Artificial Sequence
<220> FEATURE:
<223> OTHER INFORMATION: Primer

<400> SEQUENCE: 36
cttccagcca taccagtacg c                                             21

<210> SEQ ID NO 37
<211> LENGTH: 21
<212> TYPE: DNA
<213> ORGANISM: Artificial Sequence
<220> FEATURE:
<223> OTHER INFORMATION: Primer

<400> SEQUENCE: 37
gaaggtgacc aagttcatgc t                                             21

<210> SEQ ID NO 38
<211> LENGTH: 16
<212> TYPE: DNA
<213> ORGANISM: Artificial Sequence
<220> FEATURE:
<223> OTHER INFORMATION: Primer

<400> SEQUENCE: 38
gaacaatccc cggccg                                                   16

<210> SEQ ID NO 39
<211> LENGTH: 21
<212> TYPE: DNA
<213> ORGANISM: Artificial Sequence
<220> FEATURE:
<223> OTHER INFORMATION: Primer

<400> SEQUENCE: 39
gaaggtcgga gtcaacggat t                                             21

<210> SEQ ID NO 40
<211> LENGTH: 16
<212> TYPE: DNA
<213> ORGANISM: Artificial Sequence
<220> FEATURE:
<223> OTHER INFORMATION: Primer

<400> SEQUENCE: 40
gaacaatccc cggcca                                                   16

<210> SEQ ID NO 41
<211> LENGTH: 20
<212> TYPE: DNA
```

-continued

```
<213> ORGANISM: Artificial Sequence
<220> FEATURE:
<223> OTHER INFORMATION: Primer

<400> SEQUENCE: 41
cgcgtcttgc tagctgttat                                                  20

<210> SEQ ID NO 42
<211> LENGTH: 20
<212> TYPE: DNA
<213> ORGANISM: Artificial Sequence
<220> FEATURE:
<223> OTHER INFORMATION: Primer

<400> SEQUENCE: 42
gcgcgtcttg ctagctgtta                                                  20

<210> SEQ ID NO 43
<211> LENGTH: 21
<212> TYPE: DNA
<213> ORGANISM: Artificial Sequence
<220> FEATURE:
<223> OTHER INFORMATION: Primer

<400> SEQUENCE: 43
gaaggtgacc aagttcatgc t                                                21

<210> SEQ ID NO 44
<211> LENGTH: 18
<212> TYPE: DNA
<213> ORGANISM: Artificial Sequence
<220> FEATURE:
<223> OTHER INFORMATION: Primer

<400> SEQUENCE: 44
cgtttggaga agatgcat                                                    18

<210> SEQ ID NO 45
<211> LENGTH: 21
<212> TYPE: DNA
<213> ORGANISM: Artificial Sequence
<220> FEATURE:
<223> OTHER INFORMATION: Primer

<400> SEQUENCE: 45
gaaggtcgga gtcaacggat t                                                21

<210> SEQ ID NO 46
<211> LENGTH: 18
<212> TYPE: DNA
<213> ORGANISM: Artificial Sequence
<220> FEATURE:
<223> OTHER INFORMATION: Primer

<400> SEQUENCE: 46
cgtttggaga agatgcaa                                                    18

<210> SEQ ID NO 47
<211> LENGTH: 19
<212> TYPE: DNA
<213> ORGANISM: Artificial Sequence
<220> FEATURE:
<223> OTHER INFORMATION: Primer

<400> SEQUENCE: 47
atggcaattg acaaacagg                                                   19
```

-continued

```
<210> SEQ ID NO 48
<211> LENGTH: 20
<212> TYPE: DNA
<213> ORGANISM: Artificial Sequence
<220> FEATURE:
<223> OTHER INFORMATION: Primer

<400> SEQUENCE: 48
acatggcaat tgacaaacag                                              20

<210> SEQ ID NO 49
<211> LENGTH: 21
<212> TYPE: DNA
<213> ORGANISM: Artificial Sequence
<220> FEATURE:
<223> OTHER INFORMATION: Primer

<400> SEQUENCE: 49
gaaggtgacc aagttcatgc t                                            21

<210> SEQ ID NO 50
<211> LENGTH: 17
<212> TYPE: DNA
<213> ORGANISM: Artificial Sequence
<220> FEATURE:
<223> OTHER INFORMATION: Primer

<400> SEQUENCE: 50
tagctgcact tgcccaa                                                 17

<210> SEQ ID NO 51
<211> LENGTH: 21
<212> TYPE: DNA
<213> ORGANISM: Artificial Sequence
<220> FEATURE:
<223> OTHER INFORMATION: Primer

<400> SEQUENCE: 51
gaaggtcgga gtcaacggat t                                            21

<210> SEQ ID NO 52
<211> LENGTH: 17
<212> TYPE: DNA
<213> ORGANISM: Artificial Sequence
<220> FEATURE:
<223> OTHER INFORMATION: Primer

<400> SEQUENCE: 52
tagctgcact tgcccag                                                 17

<210> SEQ ID NO 53
<211> LENGTH: 20
<212> TYPE: DNA
<213> ORGANISM: Artificial Sequence
<220> FEATURE:
<223> OTHER INFORMATION: Primer

<400> SEQUENCE: 53
aaatccgcta aacagcctga                                              20

<210> SEQ ID NO 54
<211> LENGTH: 19
<212> TYPE: DNA
<213> ORGANISM: Artificial Sequence
<220> FEATURE:
```

-continued

---

<223> OTHER INFORMATION: Primer

<400> SEQUENCE: 54
aatccgctaa acagcctga                                                                                    19